(12) United States Patent
Honold et al.

(10) Patent No.: US 7,786,113 B2
(45) Date of Patent: Aug. 31, 2010

(54) HETEROCYCLIC CARBAMATE DERIVATIVES, THEIR MANUFACTURE AND USE AS PHARMACEUTICAL AGENTS

(75) Inventors: Konrad Honold, Penzberg (DE); Klaus Kaluza, Bad Heilbrunn (DE); Birgit Masjost, Basel (CH); Wolfgang Schaefer, Mannheim (DE); Stefan Scheiblich, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 12 days.

(21) Appl. No.: 11/793,750

(22) PCT Filed: Dec. 22, 2005

(86) PCT No.: PCT/EP2005/013851

§ 371 (c)(1),
(2), (4) Date: Jun. 20, 2007

(87) PCT Pub. No.: WO2006/066914

PCT Pub. Date: Jun. 29, 2006

(65) Prior Publication Data

US 2008/0009492 A1  Jan. 10, 2008

(30) Foreign Application Priority Data

Dec. 23, 2004 (EP) .................................. 04030621

(51) Int. Cl.
- *A61K 31/5377* (2006.01)
- *A61K 31/44* (2006.01)
- *C07D 413/14* (2006.01)
- *C07D 471/02* (2006.01)

(52) U.S. Cl. .................... 514/234.2; 514/303; 514/333; 544/127; 546/118; 546/256

(58) Field of Classification Search ................ 544/127; 546/118, 256; 514/234.2, 303, 333

See application file for complete search history.

(56) References Cited

U.S. PATENT DOCUMENTS

2004/0242883 A1  12/2004  Boschelli et al.

FOREIGN PATENT DOCUMENTS

| JP | 2000159760 | * | 6/2000 |
|---|---|---|---|
| WO | WO 01/00213 | | 1/2001 |
| WO | WO 01/47922 | | 7/2001 |
| WO | WO 03/035065 | | 5/2003 |
| WO | WO 2004/024897 | | 3/2004 |
| WO | WO 2005/063746 | | 7/2005 |
| WO | WO 2005/063747 | | 7/2005 |
| WO | WO 2006/066913 | | 6/2006 |

OTHER PUBLICATIONS

Sawyer et al., Expert Opin. Investig. Drugs 10 (2001) pp. 1327-1344.
Missbach et al., Bone 24 (1999) pp. 437-449.

* cited by examiner

*Primary Examiner*—Brandon J Fetterolf
*Assistant Examiner*—Anna Pagonakis
(74) *Attorney, Agent, or Firm*—George W. Johnston; Patricia S. Rocha-Tramaloni; Gene J. Yao

(57) ABSTRACT

Objects of the present invention are the compounds of formula I

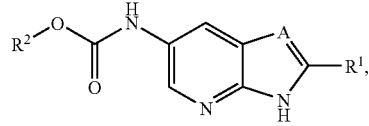

formula I their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

9 Claims, No Drawings

HETEROCYCLIC CARBAMATE DERIVATIVES, THEIR MANUFACTURE AND USE AS PHARMACEUTICAL AGENTS

This invention relates to heterocyclic carbamate derivatives that inhibit the activity of protein kinases, to a process for their manufacture, pharmaceutical compositions containing them and their manufacture as well as the use of these compounds as pharmaceutically active agents.

BACKGROUND OF THE INVENTION

Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration.

Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

The tyrosine kinases are a class of protein kinases. The Src family which consists of at least eight members (Src, Fyn, Lyn, Yes, Lck, Fgr, Hck and Blk) that participate in a variety of signaling pathways represents the major family of cytoplasmic protein tyrosine kinases (Schwartzberg, P. L., Oncogene 17 (1998) 1463-1468). The prototypical member of this tyrosine kinase family is Src, which is involved in proliferation and migration responses in many cell types (Sawyer, T., et al., Expert Opin. Investig. Drugs 10 (2001) 1327-1344). Src activity has been shown to be elevated in different cancers, e.g. breast, colon (>90%), pancreatic (>90%) and liver (>90%) tumors. Highly increased Src activity is also associated with metastasis (>90%) and poor prognosis. Antisense Src message impedes growth of colon tumor cells in nude mice (Staley, C. A., Cell Growth Differ. 8 (1997) 269-274), suggesting that Src inhibitors could slow tumor growth. Furthermore, in addition to its role in cell proliferation, Src also acts in stress response pathways, including the hypoxia response. Nude mice studies with colon tumor cells expressing antisense Src message have reduced vascularization (Ellis, L. M., et al., J. Biol. Chem. 273 (1998) 1052-1057), which suggests that Src inhibitors could be anti-angiogenic as well as anti-proliferative.

Src disrupts E-cadherin associated cell-cell interactions (Avizienyte, E., et al., Nature Cell Bio. 4 (2002) 632-638). A low molecular weight Src inhibitor prevents this disruption thereby reducing cancer cell metastasis (Nam, J. S., et al., Clin. Cancer Res. 8 (2002) 2430-2436).

Src inhibitors may prevent the secondary injury that results from a VEGF-mediated increase in vascular permeability such as that seen following stroke (Eliceiri, B. P., et al., Mol. Cell. 4 (1999) 915-924; Paul, R., et al., Nat. Med. 7 (2001) 222-227).

Blockade of Src prevents dissociation of the complex involving Flk, VE-cadherin, and β-catenin with the same kinetics with which it prevents VEGF-mediated VP/edema and account for the Src requirement in VEGF-mediated permeability and provide a basis for Src inhibition as a therapeutic option for patients with acute myocardial infarction (Weis, S., et al., J. Clin. Invest. 113 (2004) 885-894).

Src also plays a role in osteoporosis. Mice genetically engineered to be deficient in Src production were found to exhibit osteopetrosis, the failure to resorb bone (Soriano, P., et al., Cell 64 (1991) 693-702; Boyce, B. F., et al., J. Clin., Invest. 90 (1992) 1622-1627). This defect was characterized by a lack of osteoclast activity. Since osteoclasts normally express high levels of Src, inhibition of Src kinase activity may be useful in the treatment of osteoporosis (Missbach, M., et al., Bone 24 (1999) 437-449).

Low molecular weight inhibitors for protein kinases are widely known in the state of the art. For src inhibition such inhibitors are based on i.e. thieno-pyridine derivatives (US 2004/0242883); pyrido-pyrimidine derivatives (WO 04/085436); pyrido-pyrimidone derivatives (WO 04/041823); pyrimidine derivatives (WO 03/004492 and WO 01/00213); Quinazoline derivatives (WO 01/94341 and WO 02/016352); isoxazole derivatives (WO 02/083668) and pyrazole derivatives (WO 02/092573).

Some phenyl-aza-benzimidazoles are known as inhibitors of IgE-mediated immune response and suppressors of cytokines and leukocytes with antiproliferative effect from WO 04/024897. And some benzimidazole-pyrazoles and -indazoles are known as kinase inhibitors from WO 03/035065, especially as inhibitors against Kdr, Syk and Itk tyrosine kinases.

SUMMARY OF THE INVENTION

The present invention relates to benzamide derivatives of the general formula I

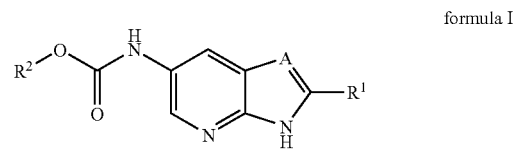

formula I wherein,

R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
or a heteroaryl group optionally substituted with halogen, nitro, amino, heterocyclyl or —Z-alkyl;
and all alkyl groups are optionally substituted one or several times by halogen, hydroxy, alkoxy, amino, alkylamino, dialkylamino or alkylsulfonyl;

X is a single bond, —NR—, —O—, —S—, —CH₂—S(O)₂ NH—, —NHS(O)₂—, —S(O)₂NH—, —S(O)₂—, —S(O)—, —NRC(O)— or —C(O)NR—;

Y is —NRC(O)— or —C(O)NR—;

Z is a single bond, —NR— or —O—;

R is hydrogen or alkyl, wherein the alkyl is optionally substituted one or several times by halogen or alkoxy;

R² is alkyl, halogenated alkyl, alkenyl, alkynyl, cycloalkyl or phenylalkyl, wherein the phenyl group is optionally substituted one or several times by halogen, alkyl, alkoxy, halogenated alkyl, halogenated alkoxy or cyano;

A is =CH— or =N—;

and all pharmaceutically acceptable salts thereof.

The compounds according to this invention show activity as protein kinase inhibitors, in particular src family tyrosine kinase inhibitors, and may therefore be useful for the treatment of diseases mediated by said tyrosine kinases.

Src family tyrosine kinase are known to be involved in a variety of disease states. Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, benign hyperplasias and cancer including colon, breast, lung and pancreatic cancer and leukemia.

Objects of the present invention are the compounds of formula I and pharmaceutically acceptable salts and their enantiomeric forms, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

DETAILED DESCRIPTION OF THE INVENTION

As used herein, the term "alkyl" means a saturated, straight-chain or branched-chain hydrocarbon containing from 1 to 4, preferably 1 or 2, carbon atoms, such as methyl, ethyl, n-propyl, isopropyl, n-butyl, 2-butyl, t-butyl.

As used herein, the term "alkoxy" means an alkyl group as defined above which is connected via an oxygen (—O—) atom.

As used herein, the term "alkylsulfonyl" means an alkyl group as defined above which is connected via —S(O)$_2$—.

As used herein, the term "acyl" means an alkyl group as defined above which is connected via a carbonyl (—C(O)—) group.

If said alkyl group is substituted one or several times by halogen, it is preferably substituted by fluorine or chlorine, especially by fluorine. Examples are difluoromethyl, trifluoromethyl, 2,2,2-trifluoroethyl, perfluorethyl and the like.

The term "halogenated alkyl" as used herein means an alkyl group as defined above which is substituted one or several times by halogen, preferably by fluorine or chlorine, especially fluorine. Examples are difluoromethyl, trifluoromethyl, 2,2,2-trifluoroethyl, 2,2,2-trifluoro-1-methyl-ethyl, perfluorethyl, and the like, preferably trifluoromethyl and 2,2,2-trifluoro-1-methyl-ethyl, especially 2,2,2-trifluoro-1-methyl-ethyl or especially trifluoromethyl.

The term "halogenated alkoxy" as used herein means an alkoxy group as defined above which is substituted one or several times by halogen, preferably by fluorine or chlorine, especially fluorine. Examples are difluoromethoxy, trifluoromethoxy, 2,2,2-trifluoroethoxy, perfluoroethoxy and the like, especially trifluoromethoxy.

The term "halogen" as used herein means fluorine, chlorine, bromine and iodine, preferably fluorine, chlorine or bromine and more preferred fluorine and chlorine.

The term "phenylalkyl" as used herein means an alkyl group as defined above, in which one of the hydrogen atoms is replaced by a phenyl group. Examples of phenylalkyl groups are benzyl, 1-phenylethyl, 2-phenylethyl, 3-phenylpropyl and the like, preferably benzyl and 1-phenylethyl.

The term "heteroaryl" means a mono- or bicyclic aromatic ring selected from pyridyl, thienyl, benzimidazolyl, pyrimidyl, thiazolyl, quinolyl, pyridazinyl, pyrazinyl, oxazolyl, quinazolinyl, indolyl, benzothiophenyl or benzofuranyl, especially from pyridyl, thienyl, benzimidazolyl, pyrimidyl, thiazolyl, quinolyl or pyridazinyl, and more preferred from pyridyl, thienyl or benzimidazolyl.

The term "cycloalkyl" means a monocyclic saturated hydrocarbon ring with 3 to 7, preferably 4 to 6 and more preferably 5 to 6, ring atoms. Examples of such saturated carbocyclic groups are cyclopropyl, cyclobutyl, cyclopentyl, cyclohexyl and cycloheptyl, preferably cyclopropyl, cyclopentyl and cyclohexyl.

In the definition of R$^1$, —Y-cycloalkyl is preferably —Y-cyclopropyl.

In the definition of R$^2$, cycloalkyl is preferably cyclopropyl, cyclobutyl, cyclopentyl or cyclohexyl; more preferably cyclopropyl, cyclopentyl or cyclohexyl and still more preferably cyclobutyl, cyclopentyl or cyclohexyl.

The term "heterocyclyl" means a saturated, monocyclic hydrocarbon ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three times, preferably one or two times by (C$_1$-C$_4$)alkyl or (C$_1$-C$_4$)acyl, which are defined as above, preferably by methyl or acetyl. Examples of such saturated heterocyclic groups are pyrrolidinyl, morpholinyl, piperazinyl, N-methyl-piperazinyl, piperidyl or N-acetyl-piperidyl and the like, preferably morpholinyl, N-methyl-piperazinyl or N-acetyl-piperidyl, more preferably morpholinyl, N-methyl-piperazinyl and still more preferably morpholinyl.

If R$^1$ is phenyl, said phenyl is optionally substituted one or several times, preferably one or two times, at the ortho, meta or para position.

If R$^1$ is heteroaryl, said heteroaryl is optionally substituted one or several times, preferably one or two times.

The compounds of formula I can exist in different tautomeric forms and in variable mixtures thereof. All tautomeric forms of the compounds of formula I and mixtures thereof are an objective of the invention. For example, if A in the definition of formula is =N—, the imidazole part of pyridyl-imidazole ring system of formula I can exist in two tautomeric forms as shown here below:

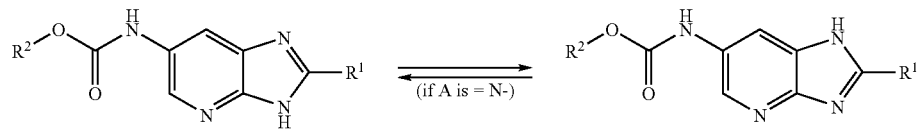

An embodiment of the invention are the compounds according to formula I, wherein A is =N—.

Another embodiment of the invention are the compounds according to formula I, wherein A is =CH—.

Another embodiment of the invention are the compounds according to formula I, wherein R$^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
  wherein the alkyl group is optionally substituted one or several times by halogen, hydroxy, alkoxy, amino, alkylamino, dialkylamino or alkylsulfonyl.

Another embodiment of the invention are the compounds according to formula I, wherein R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
  wherein the alkyl group is optionally substituted one or several times by halogen, hydroxy, alkoxy, amino, alkylamino, dialkylamino or alkylsulfanyl; and
A is =N—.

Another embodiment of the invention are the compounds according to formula I, wherein
  R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
    wherein the alkyl group is optionally substituted one or several times by halogen, hydroxy, alkoxy, amino, alkylamino, dialkylamino or alkylsulfanyl; and
  A is =CH—.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl; and
  A is =N—.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl; and
  A is =CH—.

Another embodiment of the invention are the compounds according to formula I, wherein
  R² is alkyl, halogenated alkyl, alkenyl, alkynyl or cycloalkyl.

An embodiment of the invention are the compounds according to formula I, wherein
  R² is alkyl, halogenated alkyl, alkenyl, alkynyl or cycloalkyl; and
  A is =N—.

Another embodiment of the invention are the compounds according to formula I, wherein
  R² is alkyl, halogenated alkyl, alkenyl, alkynyl or cycloalkyl; and
  A is =CH—.

Another embodiment of the invention are the compounds according to formula I, wherein
  R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
    wherein the alkyl group is optionally substituted one or several times by halogen, hydroxy, alkoxy, amino, alkylamino, dialkylamino or alkylsulfanyl; and
  R² is alkyl, halogenated alkyl, alkenyl, alkynyl or cycloalkyl.

Another embodiment of the invention are the compounds according to formula I, wherein
  R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
    wherein the alkyl group is optionally substituted one or several times by halogen, hydroxy, alkoxy, amino, alkylamino, dialkylamino or alkylsulfanyl;
  R² is alkyl, halogenated alkyl, alkenyl, alkynyl or cycloalkyl; and
  A is =N—.

Another embodiment of the invention are the compounds according to formula I, wherein
  R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl;
    wherein the alkyl group is optionally substituted one or several times by halogen, hydroxy, alkoxy, amino, alkylamino, dialkylamino or alkylsulfanyl;
  R² is alkyl, halogenated alkyl, alkenyl, alkynyl or cycloalkyl; and
  A is =CH—.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl; and
  R² is alkyl, halogenated alkyl, alkenyl, alkynyl or cycloalkyl.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl;
  R² is alkyl, halogenated alkyl, alkenyl, alkynyl or cycloalkyl; and
  A is =N—.

Another embodiment of the invention are the compounds according to formula I, wherein
  R¹ is a heteroaryl group optionally substituted with halogen, nitro, amino, heterocyclyl or —Z-alkyl;
    wherein the alkyl group is optionally substituted one or several times by halogen, hydroxy, alkoxy, amino, alkylamino, dialkylamino or alkylsulfanyl;
  R² is alkyl, halogenated alkyl, alkenyl, alkynyl or cycloalkyl; and
  A is =CH—.

Another embodiment of the invention are the compounds according to formula I, wherein
  R² is phenylalkyl,
    wherein the phenyl group is optionally substituted one or several times by halogen, alkyl, alkoxy, halogenated alkyl, halogenated alkoxy or cyano.

An embodiment of the invention are the compounds according to formula I, wherein
  R² is phenylalkyl,
    wherein the phenyl group is optionally substituted one or several times by halogen, alkyl, alkoxy, halogenated alkyl, halogenated alkoxy or cyano; and
  A is =N—.

Another embodiment of the invention are the compounds according to formula I, wherein
- $R^2$ is phenylalkyl,
  - wherein the phenyl group is optionally substituted one or several times by halogen, alkyl, alkoxy, halogenated alkyl, halogenated alkoxy or cyano; and
- A is =CH—.

Another embodiment of the invention are the compounds according to formula I, wherein
- $R^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
  - wherein the alkyl group is optionally substituted one or several times by halogen, hydroxy, alkoxy, amino, alkylamino, dialkylamino or alkylsulfanyl; and
- $R^2$ is phenylalkyl,
  - wherein the phenyl group is optionally substituted one or several times by halogen, alkyl, alkoxy, halogenated alkyl, halogenated alkoxy or cyano.

Another embodiment of the invention are the compounds according to formula I, wherein
- $R^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
  - wherein the alkyl group is optionally substituted one or several times by halogen, hydroxy, alkoxy, amino, alkylamino, dialkylamino or alkylsulfanyl;
- $R^2$ is phenylalkyl,
  - wherein the phenyl group is optionally substituted one or several times by halogen, alkyl, alkoxy, halogenated alkyl, halogenated alkoxy or cyano; and
- A is =N—.

Another embodiment of the invention are the compounds according to formula I, wherein
- $R^1$ is a phenyl group optionally substituted with halogen, cyano, nitro, amino, —C(O)OH, heterocyclyl, —O-heterocyclyl, —S(O)$_2$NH$_2$, —X-alkyl or —Y-cycloalkyl;
  - wherein the alkyl group is optionally substituted one or several times by halogen, hydroxy, alkoxy, amino, alkylamino, dialkylamino or alkylsulfanyl;
- $R^2$ is phenylalkyl,
  - wherein the phenyl group is optionally substituted one or several times by halogen, alkyl, alkoxy, halogenated alkyl, halogenated alkoxy or cyano; and
- A is =CH—.

Another embodiment of the invention are the compounds according to formula I, wherein
- $R^1$ is a heteroaryl group optionally substituted with halogen, nitro, amino, heterocyclyl or —Z-alkyl;
  - wherein the alkyl group is optionally substituted one or several times by halogen, hydroxy, alkoxy, amino, alkylamino, dialkylamino or alkylsulfanyl; and
- $R^2$ is phenylalkyl,
  - wherein the phenyl group is optionally substituted one or several times by halogen, alkyl, alkoxy, halogenated alkyl, halogenated alkoxy or cyano.

Another embodiment of the invention are the compounds according to formula I, wherein
- $R^1$ is a heteroaryl group optionally substituted with halogen, nitro, amino, heterocyclyl or —Z-alkyl;
  - wherein the alkyl group is optionally substituted one or several times by halogen, hydroxy, alkoxy, amino, alkylamino, dialkylamino or alkylsulfanyl;
- $R^2$ is phenylalkyl,
  - wherein the phenyl group is optionally substituted one or several times by halogen, alkyl, alkoxy, halogenated alkyl, halogenated alkoxy or cyano; and
- A is =N—.

Another embodiment of the invention are the compounds according to formula I, wherein
- $R^1$ is a heteroaryl group optionally substituted with halogen, nitro, amino, heterocyclyl or —Z-alkyl;
  - wherein the alkyl group is optionally substituted one or several times by halogen, hydroxy, alkoxy, amino, alkylamino, dialkylamino or alkylsulfanyl;
- $R^2$ is phenylalkyl,
  - wherein the phenyl group is optionally substituted one or several times by halogen, alkyl, alkoxy, halogenated alkyl, halogenated alkoxy or cyano; and
- A is =CH—.

Another embodiment of the invention are the compounds according to formula I, wherein
- $R^1$ is a phenyl group.

Another embodiment of the invention are the compounds according to formula I, wherein
- $R^1$ is a phenyl group; and
- A is =N—.

Another embodiment of the invention are the compounds according to formula I, wherein
- $R^1$ is a phenyl group; and
- A is =CH—.

Another embodiment of the invention are the compounds according to formula I, wherein
- $R^1$ is a phenyl group; and
- $R^2$ is alkyl or halogenated alkyl; and
- A is =N—.

Such compounds, for example, may be selected from the group consisting of:
(2-Phenyl-1H-imidazo[4,5-b]pyridin-6-yl)-carbamic acid isopropyl ester;
(2-Phenyl-3H-imidazo[4,5-b]pyridin-6-yl)-carbamic acid isobutyl ester;
(2-Phenyl-1H-imidazo[4,5-b]pyridin-6-yl)-carbamic acid propyl ester;
(2-Phenyl-3H-imidazo[4,5-b]pyridin-6-yl)-carbamic acid tert-butyl ester;
(2-Phenyl-3H-imidazo[4,5-b]pyridin-6-yl)-carbamic acid 2,2-dimethyl-propyl ester;
(2-Phenyl-3H-imidazo[4,5-b]pyridin-6-yl)-carbamic acid 1-ethyl-propyl ester;
(2-Phenyl-3H-imidazo[4,5-b]pyridin-6-yl)-carbamic acid sec-butyl ester;
(2-Phenyl-3H-imidazo[4,5-b]pyridin-6-yl)-carbamic acid ethyl ester; and
(2-Phenyl-3H-imidazo[4,5-b]pyridin-6-yl)-carbamic acid 2,2,2-trifluoro-1-methyl-ethyl ester.

Another embodiment of the invention are the compounds according to formula I, wherein
- $R^1$ is a phenyl group; and
- $R^2$ is alkyl or halogenated alkyl; and
- A is =CH—.

Such compounds, for example, may be selected from the group consisting of:
(2-Phenyl-1H-pyrrolo[2,3-b]pyridin-5-yl)-carbamic acid isopropyl ester;
(2-Phenyl-1H-pyrrolo[2,3-b]pyridin-5-yl)-carbamic acid 2,2-dimethyl-propyl ester;
(2-Phenyl-1H-pyrrolo[2,3-b]pyridin-5-yl)-carbamic acid ethyl ester; and (2-Phenyl-1H-pyrrolo[2,3-b]pyridin-5-yl)-carbamic acid isobutyl ester.

Another embodiment of the invention are the compounds according to formula I, wherein
$R^1$ is a phenyl group; and
$R^2$ is alkenyl or alkynyl; and
A is =N—.

Such compounds, for example, may be selected from the group consisting of:
(2-Phenyl-3H-imidazo[4,5-b]pyridin-6-yl)-carbamic acid allyl ester; and
(2-Phenyl-3H-imidazo[4,5-b]pyridin-6-yl)-carbamic acid 1-methyl-allyl ester.

Another embodiment of the invention are the compounds according to formula I, wherein
$R^1$ is a phenyl group; and
$R^2$ is alkenyl or alkynyl; and
A is =CH—.

Such compounds, for example, may be selected from the group consisting of:
(2-Phenyl-1H-pyrrolo[2,3-b]pyridin-5-yl)-carbamic acid allyl ester.

Another embodiment of the invention are the compounds according to formula I, wherein
$R^1$ is a phenyl group; and
$R^2$ is cycloalkyl; and
A is =N—.

Such compounds, for example, may be selected from the group consisting of:
(2-Phenyl-3H-imidazo[4,5-b]pyridin-6-yl)-carbamic acid cyclopentyl ester; and
(2-Phenyl-3H-imidazo[4,5-b]pyridin-6-yl)-carbamic acid cyclohexyl ester.

Another embodiment of the invention are the compounds according to formula I, wherein
$R^1$ is a phenyl group; and
$R^2$ is cycloalkyl; and
A is =CH—.

Another embodiment of the invention are the compounds according to formula I, wherein
$R^1$ is a phenyl group; and
$R^2$ is phenylalkyl,
 wherein the phenyl group is optionally substituted one or several times by halogen, alkyl, alkoxy, halogenated alkyl, halogenated alkoxy or cyano; and
A is =N—.

Such a compound is for example:
(2-Phenyl-3H-imidazo[4,5-b]pyridin-6-yl)-carbamic acid 1-phenyl-ethyl ester.

Another embodiment of the invention are the compounds according to formula I, wherein
$R^1$ is a phenyl group; and
$R^2$ is phenylalkyl,
 wherein the phenyl group is optionally substituted one or several times by halogen, alkyl, alkoxy, halogenated alkyl, halogenated alkoxy or cyano; and
A is =CH—.

Such a compound is for example:
(2-Phenyl-1H-pyrrolo[2,3-b]pyridin-5-yl)-carbamic acid benzyl ester; and
(2-Phenyl-1H-pyrrolo[2,3-b]pyridin-5-yl)-carbamic acid 2-chloro-benzyl ester.

Another embodiment of the invention are the compounds according to formula I, wherein
$R^1$ is a phenyl group substituted with halogen, cyano, nitro, amino, —C(O)OH or —S(O)$_2$NH$_2$ Another embodiment of the invention are the compounds according to formula I, wherein
$R^1$ is a phenyl group substituted with halogen, cyano, nitro, amino, —C(O)OH or —S(O)$_2$NH$_2$; and
A is =N—.

Another embodiment of the invention are the compounds according to formula I, wherein
$R^1$ is a phenyl group substituted with halogen, cyano, nitro, amino, —C(O)OH or —S(O)$_2$NH$_2$; and
A is =CH—.

Another embodiment of the invention are the compounds according to formula I, wherein
$R^1$ is a phenyl group substituted with halogen, cyano, nitro, amino, —C(O)OH or —S(O)$_2$NH$_2$;
$R^2$ is alkyl; and
A is =N—.

Such compounds, for example, may be selected from the group consisting of:
[2-(4-Sulfamoyl-phenyl)-3H-imidazo[4,5-b]pyridin-6-yl]-carbamic acid isopropyl ester;
[2-(4-Nitro-phenyl)-3H-imidazo[4,5-b]pyridin-6-yl]-carbamic acid isopropyl ester;
[2-(4-Amino-phenyl)-3H-imidazo[4,5-b]pyridin-6-yl]-carbamic acid isopropyl ester;
[2-(3-Nitro-phenyl)-3H-imidazo[4,5-b]pyridin-6-yl]-carbamic acid isopropyl ester; and
[2-(3-Amino-phenyl)-3H-imidazo[4,5-b]pyridin-6-yl]-carbamic acid isopropyl ester.

Another embodiment of the invention are the compounds according to formula I, wherein
$R^1$ is a phenyl group substituted with halogen, cyano, nitro, amino, —C(O)OH or —S(O)$_2$NH$_2$;
$R^2$ is alkyl; and
A is =CH—.

Another embodiment of the invention are the compounds according to formula I, wherein
$R^1$ is a phenyl group substituted with halogen, cyano, nitro, amino, —C(O)OH or —S(O)$_2$NH$_2$; and
$R^2$ is alkyl.

Another embodiment of the invention are the compounds according to formula I, wherein
$R^1$ is a phenyl group substituted with heterocyclyl or —O-heterocyclyl.

Another embodiment of the invention are the compounds according to formula I, wherein
$R^1$ is a phenyl group substituted with heterocyclyl or —O-heterocyclyl; and
A is =N—.

Another embodiment of the invention are the compounds according to formula I, wherein
$R^1$ is a phenyl group substituted with heterocyclyl or —O-heterocyclyl; and
A is =CH—.

Another embodiment of the invention are the compounds according to formula I, wherein
$R^1$ is a phenyl group substituted with heterocyclyl or —O-heterocyclyl;
$R^2$ is alkyl; and
A is =N—.

Such a compound is for example:
[2-(4-Morpholin-4-yl-phenyl)-3H-imidazo[4,5-b]pyridin-6-yl]-carbamic acid isopropyl ester.

Another embodiment of the invention are the compounds according to formula I, wherein $R^1$ is a phenyl group substituted with heterocyclyl or —O-heterocyclyl;
$R^2$ is alkyl; and
A is =CH—.

Another embodiment of the invention are the compounds according to formula I, wherein
$R^1$ is a phenyl group substituted with heterocyclyl or —O-heterocyclyl; and
$R^2$ is alkyl.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfonyl.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl; and
A is =N—.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl; and
A is =CH—.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl; and
$R^2$ is alkyl.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl;
X is a single bond, —NR—, —O— or —S—;
$R^2$ is alkyl; and
A is =N—.

Such compounds, for example, may be selected from the group consisting of:
{2-[4-(2-Methoxy-ethoxy)-phenyl]-3H-imidazo[4,5-b]pyridin-6-yl}-carbamic acid isopropyl ester;
{2-[3-(2-Methoxy-ethoxy)-phenyl]-3H-imidazo[4,5-b]pyridin-6-yl}-carbamic acid isopropyl ester;
{2-[4-(2-Diethylamino-ethoxy)-phenyl]-3H-imidazo[4,5-b]pyridin-6-yl}-carbamic acid isopropyl ester;
{2-[4-(2-Diethylamino-ethoxy)-phenyl]-3H-imidazo[4,5-b]pyridin-6-yl}-carbamic acid isopropyl ester; acetic acid salt;
[2-(4-Methylsulfanyl-phenyl)-3H-imidazo[4,5-b]pyridin-6-yl]-carbamic acid isopropyl ester; and
[2-(3-Methylsulfanyl-phenyl)-3H-imidazo[4,5-b]pyridin-6-yl]-carbamic acid isopropyl ester.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl;
X is a single bond, —NR—, —O— or —S—;
$R^2$ is alkyl; and
A is =CH—.

Such compounds, for example, may be selected from the group consisting of:
{2-[3-(2-Methoxy-ethoxy)-phenyl]-1H-pyrrolo[2,3-b]pyridin-5-yl}-carbamic acid ethyl ester;
{2-[3-(2-Methoxy-ethoxy)-phenyl]-1H-pyrrolo[2,3-b]pyridin-5-yl}-carbamic acid isopropyl ester;
{2-[3-(2-Methoxy-ethoxy)-phenyl]-1H-pyrrolo[2,3-b]pyridin-5-yl}-carbamic acid isobutyl ester; and
{2-[3-(2-Methoxy-ethoxy)-phenyl]-1H-pyrrolo[2,3-b]pyridin-5-yl}-carbamic acid 2,2-dimethyl-propyl ester.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl;
X is —NRC(O)—, —C(O)NR—, —CH$_2$—S(O)$_2$NH—, —S(O)$_2$NH—, —NHS(O)$_2$—, —S(O)$_2$— or —S(O)—;
$R^2$ is alkyl; and
A is =N—.

Such compounds, for example, may be selected from the group consisting of:
[2-(3-Acetylamino-phenyl)-3H-imidazo[4,5-b]pyridin-6-yl]-carbamic acid isopropyl ester;
[2-(3-Methanesulfonylamino-phenyl)-3H-imidazo[4,5-b]pyridin-6-yl]-carbamic acid isopropyl ester; and
[2-(3-Methylsulfinyl-phenyl)-3H-imidazo[4,5-b]pyridin-6-yl]-carbamic acid isopropyl ester.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl;
X is —NRC(O)—, —C(O)NR—, —CH$_2$—S(O)$_2$NH—, —S(O)$_2$NH—, —NHS(O)$_2$—, —S(O)$_2$— or —S(O)—;
$R^2$ is alkyl; and
A is =CH—.

Such compounds, for example, may be selected from the group consisting of:
[2-(3-Acetylamino-phenyl)-1H-pyrrolo[2,3-b]pyridin-5-yl]-carbamic acid 2,2-dimethyl-propyl ester;
[2-(4-Acetylamino-phenyl)-1H-pyrrolo[2,3-b]pyridin-5-yl]-carbamic acid 2,2-dimethyl-propyl ester;
[2-(3-Acetylamino-phenyl)-1H-pyrrolo[2,3-b]pyridin-5-yl]-carbamic acid ethyl ester;
[2-(3-Acetylamino-phenyl)-1H-pyrrolo[2,3-b]pyridin-5-yl]-carbamic acid isopropyl ester; and
[2-(3-Acetylamino-phenyl)-1H-pyrrolo[2,3-b]pyridin-5-yl]-carbamic acid isobutyl ester.

Another embodiment of the invention are the compounds according to formula I, wherein
$R^1$ is a phenyl group optionally substituted with —X-alkyl; wherein the alkyl group are optionally substituted one or several times by halogen, hydroxy, alkoxy, amino, alkylamino, dialkylamino or alkylsulfanyl;
X is a single bond, —NR—, —O— or —S—;
$R^2$ is alkenyl; and
A is =CH—.

Such a compound is for example:
{2-[3-(2-Methoxy-ethoxy)-phenyl]-1H-pyrrolo[2,3-b]pyridin-5-yl}-carbamic acid allyl ester.

Another embodiment of the invention are the compounds according to formula I, wherein
- $R^1$ is a phenyl group optionally substituted with —X-alkyl;
  wherein the alkyl group are optionally substituted one or several times by halogen, hydroxy, alkoxy, amino, alkylamino, dialkylamino or alkylsulfanyl;
- X is —NRC(O)—, —C(O)NR—, —CH$_2$—S(O)$_2$NH—, —S(O)$_2$NH—, —NHS(O)$_2$—, —S(O)$_2$— or —S(O)—;
- $R^2$ is alkenyl; and
- A is =CH—.

Such compounds, for example, may be selected from the group consisting of:
[2-(3-Acetylamino-phenyl)-1H-pyrrolo[2,3-b]pyridin-5-yl]-carbamic acid allyl ester; and
[2-(4-Acetylamino-phenyl)-1H-pyrrolo[2,3-b]pyridin-5-yl]-carbamic acid allyl ester.

Another embodiment of the invention are the compounds according to formula I, wherein
- $R^1$ is a phenyl group optionally substituted with —X-alkyl;
  wherein the alkyl group are optionally substituted one or several times by halogen, hydroxy, alkoxy, amino, alkylamino, dialkylamino or alkylsulfanyl;
- X is a single bond, —NR—, —O— or —S—;
- $R^2$ is phenylalkyl,
  wherein the phenyl group is optionally substituted one or several times by halogen, alkyl, alkoxy, halogenated alkyl, halogenated alkoxy or cyano; and
- A is =CH—.

Such compounds, for example, may be selected from the group consisting of:
{2-[3-(2-Methoxy-ethoxy)-phenyl]-1H-pyrrolo[2,3-b]pyridin-5-yl}-carbamic acid 2-chloro-benzyl ester; and
{2-[3-(2-Methoxy-ethoxy)-phenyl]-1H-pyrrolo[2,3-b]pyridin-5-yl}-carbamic acid benzyl ester.

Another embodiment of the invention are the compounds according to formula I, wherein
- $R^1$ is a phenyl group optionally substituted with —X-alkyl;
  wherein the alkyl group are optionally substituted one or several times by halogen, hydroxy, alkoxy, amino, alkylamino, dialkylamino or alkylsulfanyl;
- X is —NRC(O)—, —C(O)NR—, —CH$_2$—S(O)$_2$NH—, —S(O)$_2$NH—, NHS(O)$_2$—, —S(O)$_2$— or —S(O)—;
- $R^2$ is phenylalkyl,
  wherein the phenyl group is optionally substituted one or several times by halogen, alkyl, alkoxy, halogenated alkyl, halogenated alkoxy or cyano; and
- A is =CH—.

Such compounds, for example, may be selected from the group consisting of:
[2-(3-Acetylamino-phenyl)-1H-pyrrolo[2,3-b]pyridin-5-yl]-carbamic acid 2-chloro-benzyl ester; and
[2-(3-Acetylamino-phenyl)-1H-pyrrolo[2,3-b]pyridin-5-yl]-carbamic acid benzyl ester.

Another embodiment of the invention are the compounds according to formula I, wherein
- $R^1$ is a phenyl group optionally substituted with —Y-cycloalkyl.

Another embodiment of the invention are the compounds according to formula I, wherein
- $R^1$ is a phenyl group optionally substituted with —Y-cycloalkyl; and
- A is =N—.

Another embodiment of the invention are the compounds according to formula I, wherein

- $R^1$ is a phenyl group optionally substituted with —Y-cycloalkyl; and
- A is =CH—.

Another embodiment of the invention are the compounds according to formula I, wherein
- $R^1$ is a phenyl group optionally substituted with —Y-cycloalkyl;
- $R^2$ is alkyl.

Another embodiment of the invention are the compounds according to formula I, wherein
- $R^1$ is a phenyl group optionally substituted with —Y-cycloalkyl;
- $R^2$ is alkyl; and
- A is =N—.

Another embodiment of the invention are the compounds according to formula I, wherein
- $R^1$ is a phenyl group optionally substituted with —Y-cycloalkyl;
- $R^2$ is alkyl; and
- A is =CH—.

Another embodiment of the invention are the compounds according to formula I, wherein
- $R^1$ is a pyridyl, thienyl or benzimidazolyl group optionally substituted with halogen, nitro, amino, heterocyclyl or —Z-alkyl;
  wherein the alkyl group is optionally substituted one or several times by halogen, hydroxy, alkoxy, amino, alkylamino, dialkylamino or alkylsulfanyl.

Another embodiment of the invention are the compounds according to formula I, wherein
- $R^1$ is a pyridyl, thienyl or benzimidazolyl group optionally substituted with halogen, nitro, amino, heterocyclyl or —Z-alkyl;
  wherein the alkyl group is optionally substituted one or several times by halogen, hydroxy, alkoxy, amino, alkylamino, dialkylamino or alkylsulfonyl; and
- A is =N—.

Another embodiment of the invention are the compounds according to formula I, wherein
- $R^1$ is a pyridyl, thienyl or benzimidazolyl group optionally substituted with halogen, nitro, amino, heterocyclyl or —Z-alkyl;
  wherein the alkyl group is optionally substituted one or several times by halogen, hydroxy, alkoxy, amino, alkylamino, dialkylamino or alkylsulfonyl; and
- A is =CH—.

Another embodiment of the invention are the compounds according to formula I, wherein
- $R^1$ is a pyridyl group optionally substituted with halogen, nitro, amino, heterocyclyl or —Z-alkyl;
  wherein the alkyl group is optionally substituted one or several times by halogen, hydroxy, alkoxy, amino, alkylamino, dialkylamino or alkylsulfonyl; and
- $R^2$ is alkyl.

Another embodiment of the invention are the compounds according to formula I, wherein
- $R^1$ is a pyridyl group optionally substituted with halogen, nitro, amino, heterocyclyl or —Z-alkyl;
  wherein the alkyl group is optionally substituted one or several times by halogen, hydroxy, alkoxy, amino, alkylamino, dialkylamino or alkylsulfonyl; and
- $R^2$ is alkyl; and
- A is =N—.

Such compounds, for example, may be selected from the group consisting of:
[2-(6-Methyl-pyridin-3-yl)-3H-imidazo[4,5-b]pyridin-6-yl]-carbamic acid isopropyl ester; and

[2-(2-Methyl-pyridin-4-yl)-3H-imidazo[4,5-b]pyridin-6-yl]-carbamic acid isopropyl ester.

Another embodiment of the invention are the compounds according to formula I, wherein
- $R^1$ is a pyridyl group optionally substituted with halogen, nitro, amino, heterocyclyl or —Z-alkyl;
  - wherein the alkyl group is optionally substituted one or several times by halogen, hydroxy, alkoxy, amino, alkylamino, dialkylamino or alkylsulfonyl;
- $R^2$ is alkyl; and
- A is =CH—.

Another embodiment of the invention are the compounds according to formula I, wherein
- $R^1$ is a thienyl or benzimidazolyl group optionally substituted with —Z-alkyl;
- Z is a single bond; and
- $R^2$ is alkyl.

Another embodiment of the invention are the compounds according to formula I, wherein
- $R^1$ is a thienyl or benzimidazolyl group optionally substituted with —Z-alkyl;
- Z is a single bond;
- $R^2$ is alkyl; and
- A is =N—.

Such compounds, for example, may be selected from the group consisting of:
[2-(1H-Benzoimidazol-5-yl)-3H-imidazo[4,5-b]pyridin-6-yl]-carbamic acid isopropyl ester;
[2-(1H-Benzoimidazol-5-yl)-3H-imidazo[4,5-b]pyridin-6-yl]-carbamic acid isopropyl ester; acetic acid salt;
[2-(1H-Benzoimidazol-5-yl)-3H-imidazo[4,5-b]pyridin-6-yl]-carbamic acid isopropyl ester; hydrogen chloride salt;
(2-Thiophen-2-yl-3H-imidazo[4,5-b]pyridin-6-yl)-carbamic acid isopropyl ester; and
(2-Thiophen-3-yl-3H-imidazo[4,5-b]pyridin-6-yl)-carbamic acid isopropyl ester.

Another embodiment of the invention are the compounds according to formula I, wherein
- $R^1$ is a thienyl or benzimidazolyl group optionally substituted with —Z-alkyl;
- Z is a single bond;
- $R^2$ is alkyl; and
- A is =CH—.

Another embodiment of the invention are the compounds according to formula I, wherein
- $R^1$ is a phenyl group optionally substituted one to three, preferably one or two times with halogen, nitro, amino, —C(O)OH, heterocyclyl, —S(O)$_2$NH$_2$, —X-alkyl;
  - or a heteroaryl group optionally substituted one or two times with halogen, heterocyclyl or —Z-alkyl;
  - and all alkyl groups are optionally substituted one or two times by hydroxy, alkoxy or dialkylamino;
- X is —NR—, —O—, —S—, —NHS(O)$_2$—, —S(O)$_2$—, —S(O)—, —NRC(O)— or —C(O)NR—;
- Z is a single bond or —NR—;
- R is hydrogen or alkyl, wherein the alkyl is optionally substituted one or two times by alkoxy; and
- $R^2$ is alkyl, halogenated alkyl, alkenyl, alkynyl, cycloalkyl or phenylalkyl, wherein the phenyl group is optionally substituted one or two times by halogen.

Such compounds, for example, may be selected from the group consisting of:
(2-Phenyl-3H-imidazo[4,5-b]pyridin-6-yl)-carbamic acid 1-methyl-prop-2-ynyl ester;
(2-Phenyl-3H-imidazo[4,5-b]pyridin-6-yl)-carbamic acid 1-methyl-but-2-ynyl ester;
(2-Phenyl-3H-imidazo[4,5-b]pyridin-6-yl)-carbamic acid cyclobutyl ester;
(2-Phenyl-3H-imidazo[4,5-b]pyridin-6-yl)-carbamic acid 1,3-dimethyl-butyl ester;
(2-Phenyl-3H-imidazo[4,5-b]pyridin-6-yl)-carbamic acid 1,2-dimethyl-propyl ester;
{2-[3-(3-Methoxy-propionylamino)-phenyl]-3H-imidazo[4,5-b]pyridin-6-yl}-carbamic acid isopropyl ester;
(2-Phenyl-3H-imidazo[4,5-b]pyridin-6-yl)-carbamic acid (E)-1-methyl-but-2-enyl ester;
(2-Phenyl-3H-imidazo[4,5-b]pyridin-6-yl)-carbamic acid 1,2-dimethyl-allyl ester
{2-[4-(4-Methyl-piperazin-1-yl)-phenyl]-3H-imidazo[4,5-b]pyridin-6-yl}-carbamic acid isopropyl ester;
{2-[3-(2-Hydroxy-ethyl)-phenyl]-3H-imidazo[4,5-b]pyridin-6-yl}-carbamic acid isopropyl ester;
[2-(6-Morpholin-4-yl-pyridin-3-yl)-3H-imidazo[4,5-b]pyridin-6-yl]-carbamic acid isopropyl ester;
[2-(4-Methanesulfonyl-phenyl)-3H-imidazo[4,5-b]pyridin-6-yl]-carbamic acid isopropyl ester;
[2-(4-Methanesulfinyl-phenyl)-3H-imidazo[4,5-b]pyridin-6-yl]-carbamic acid isopropyl ester;
[2-(3-Methylsulfonyl-phenyl)-3H-imidazo[4,5-b]pyridin-6-yl]-carbamic acid isopropyl ester;
[2-(3,4-Difluoro-phenyl)-3H-imidazo[4,5-b]pyridin-6-yl]-carbamic acid isopropyl ester;
(2-{4-[Bis-(2-methoxy-ethyl)-amino]-3-fluoro-phenyl}-3H-imidazo[4,5-b]pyridin-6-yl)-carbamic acid isopropyl ester;
3-(6-Isopropoxycarbonylamino-3H-imidazo[4,5-b]pyridin-2-yl)-benzoic acid;
{2-[3-(2-Methoxy-1-methoxymethyl-ethylcarbamoyl)-phenyl]-3H-imidazo[4,5-b]pyridin-6-yl}-carbamic acid isopropyl ester;
{2-[3-(3-Methoxy-propylcarbamoyl)-phenyl]-3H-imidazo[4,5-b]pyridin-6-yl}-carbamic acid isopropyl ester;
[2-(2-Chloro-pyridin-4-yl)-3H-imidazo[4,5-b]pyridin-6-yl]-carbamic acid isopropyl ester; and
{2-[2-(3-Methoxy-propylamino)-pyridin-4-yl]-3H-imidazo[4,5-b]pyridin-6-yl}-carbamic acid isopropyl ester.

Another embodiment of the invention are the compounds according to formula I, wherein
- $R^1$ is a phenyl group optionally substituted one to three, preferably one or two times with —X-alkyl; wherein the alkyl group is optionally substituted one or two times by alkoxy;
- X is —O— or —NRC(O)—;
- R is hydrogen;
- $R^2$ is alkyl, alkenyl or phenylalkyl, wherein the phenyl group is optionally substituted one or two times by chlorine; and
- A is =CH—.

Such compounds, for example, may be selected from the group consisting of:
(2-Phenyl-TH-pyrrolo[2,3-b]pyridin-5-yl)-carbamic acid isopropyl ester;
{2-[3-(2-Methoxy-ethoxy)-phenyl]-1H-pyrrolo[2,3-b]pyridin-5-yl}-carbamic acid isopropyl ester;
(2-Phenyl-1H-pyrrolo[2,3-b]pyridin-5-yl)-carbamic acid 2,2-dimethyl-propyl ester;
{2-[4-(2-Methoxy-ethoxy)-phenyl]-1H-pyrrolo[2,3-b]pyridin-5-yl}-carbamic acid ethyl ester;
{2-[4-(2-Methoxy-ethoxy)-phenyl]-1H-pyrrolo[2,3-b]pyridin-5-yl}-carbamic acid allyl ester;
{2-[3-(2-Methoxy-ethoxy)-phenyl]-1H-pyrrolo[2,3-b]pyridin-5-yl}-carbamic acid ethyl ester;

{2-[3-(2-Methoxy-ethoxy)-phenyl]-1H-pyrrolo[2,3-b]pyridin-5-yl}-carbamic acid allyl ester;
(2-Phenyl-1H-pyrrolo[2,3-b]pyridin-5-yl)-carbamic acid benzyl ester;
{2-[3-(2-Methoxy-ethoxy)-phenyl]-1H-pyrrolo[2,3-b]pyridin-5-yl}-carbamic acid isobutyl ester;
{2-[3-(2-Methoxy-ethoxy)-phenyl]-1H-pyrrolo[2,3-b]pyridin-5-yl}-carbamic acid 2-chloro-benzyl ester;
(2-Phenyl-1H-pyrrolo[2,3-b]pyridin-5-yl)-carbamic acid ethyl ester;
(2-Phenyl-1H-pyrrolo[2,3-b]pyridin-5-yl)-carbamic acid 2-chloro-benzyl ester;
(2-Phenyl-1H-pyrrolo[2,3-b]pyridin-5-yl)-carbamic acid allyl ester;
(2-Phenyl-1H-pyrrolo[2,3-b]pyridin-5-yl)-carbamic acid isobutyl ester;
{2-[3-(2-Methoxy-ethoxy)-phenyl]-1H-pyrrolo[2,3-b]pyridin-5-yl}-carbamic acid 2,2-dimethyl-propyl ester;
{2-[3-(2-Methoxy-ethoxy)-phenyl]-1H-pyrrolo[2,3-b]pyridin-5-yl}-carbamic acid benzyl ester;
{2-[4-(2-Methoxy-ethoxy)-phenyl]-1H-pyrrolo[2,3-b]pyridin-5-yl}-carbamic acid isopropyl ester;
{2-[4-(2-Methoxy-ethoxy)-phenyl]-1H-pyrrolo[2,3-b]pyridin-5-yl}-carbamic acid benzyl ester;
{2-[4-(2-Methoxy-ethoxy)-phenyl]-1H-pyrrolo[2,3-b]pyridin-5-yl}-carbamic acid isobutyl ester;
[2-(3-Acetylamino-phenyl)-1H-pyrrolo[2,3-b]pyridin-5-yl]-carbamic acid isopropyl ester;
[2-(4-Acetylamino-phenyl)-1H-pyrrolo[2,3-b]pyridin-5-yl]-carbamic acid allyl ester;
[2-(3-Acetylamino-phenyl)-1H-pyrrolo[2,3-b]pyridin-5-yl]-carbamic acid 2-chloro-benzyl ester;
[2-(3-Acetylamino-phenyl)-1H-pyrrolo[2,3-b]pyridin-5-yl]-carbamic acid benzyl ester;
[2-(3-Acetylamino-phenyl)-1H-pyrrolo[2,3-b]pyridin-5-yl]-carbamic acid 2,2-dimethyl-propyl ester;
[2-(4-Acetylamino-phenyl)-1H-pyrrolo[2,3-b]pyridin-5-yl]-carbamic acid 2,2-dimethyl-propyl ester;
[2-(3-Acetylamino-phenyl)-1H-pyrrolo[2,3-b]pyridin-5-yl]-carbamic acid ethyl ester;
[2-(3-Acetylamino-phenyl)-1H-pyrrolo[2,3-b]pyridin-5-yl]-carbamic acid allyl ester; and
[2-(3-Acetylamino-phenyl)-1H-pyrrolo[2,3-b]pyridin-5-yl]-carbamic acid isobutyl ester.

Another embodiment of the invention are the compounds according to formula I, wherein
- $R^1$ is a phenyl group optionally substituted one to three, preferably one or two times with fluorine, nitro, amino, —C(O)OH, heterocyclyl, —S(O)$_2$NH$_2$, —X-alkyl; wherein the alkyl group is optionally substituted one or two times by hydroxy, alkoxy or dialkylamino;
- X is —NR—, —O—, —S—, —NHS(O)$_2$—, —S(O)$_2$—, —S(O)—, —NRC(O)— or —C(O)NR—;
- R is hydrogen or alkyl, wherein the alkyl is optionally substituted one or two times by alkoxy;
- $R^2$ is alkyl, halogenated alkyl, alkenyl, alkynyl, cycloalkyl or phenylalkyl, wherein the phenyl group is optionally substituted one or two times by halogen; and
- A is =N—.

Such compounds, for example, may be selected from the group consisting of:
(2-Phenyl-3H-imidazo[4,5-b]pyridin-6-yl)-carbamic acid 1-methyl-allyl ester;
(2-Phenyl-1H-imidazo[4,5-b]pyridin-6-yl)-carbamic acid isopropyl ester;
(2-Phenyl-3H-imidazo[4,5-b]pyridin-6-yl)-carbamic acid cyclohexyl ester;
(2-Phenyl-3H-imidazo[4,5-b]pyridin-6-yl)-carbamic acid isobutyl ester;
(2-Phenyl-3H-imidazo[4,5-b]pyridin-6-yl)-carbamic acid allyl ester;
(2-Phenyl-3H-imidazo[4,5-b]pyridin-6-yl)-carbamic acid tert-butyl ester;
(2-Phenyl-3H-imidazo[4,5-b]pyridin-6-yl)-carbamic acid cyclopentyl ester;
(2-Phenyl-3H-imidazo[4,5-b]pyridin-6-yl)-carbamic acid ethyl ester;
(2-Phenyl-3H-imidazo[4,5-b]pyridin-6-yl)-carbamic acid sec-butyl ester;
(2-Phenyl-3H-imidazo[4,5-b]pyridin-6-yl)-carbamic acid 1-ethyl-propyl ester;
(2-Phenyl-3H-imidazo[4,5-b]pyridin-6-yl)-carbamic acid 2,2,2-trifluoro-1-methyl-ethyl ester;
(2-Phenyl-3H-imidazo[4,5-b]pyridin-6-yl)-carbamic acid 2,2-dimethyl-propyl ester;
(2-Phenyl-3H-imidazo[4,5-b]pyridin-6-yl)-carbamic acid 1-phenyl-ethyl ester;
(2-Phenyl-1H-imidazo[4,5-b]pyridin-6-yl)-carbamic acid propyl ester;
(2-Phenyl-3H-imidazo[4,5-b]pyridin-6-yl)-carbamic acid 1-methyl-prop-2-ynyl ester;
(2-Phenyl-3H-imidazo[4,5-b]pyridin-6-yl)-carbamic acid 1-methyl-but-2-ynyl ester;
(2-Phenyl-3H-imidazo[4,5-b]pyridin-6-yl)-carbamic acid cyclobutyl ester;
(2-Phenyl-3H-imidazo[4,5-b]pyridin-6-yl)-carbamic acid 1,3-dimethyl-butyl ester;
(2-Phenyl-3H-imidazo[4,5-b]pyridin-6-yl)-carbamic acid 1,2-dimethyl-propyl ester;
{2-[3-(3-Methoxy-propionylamino)-phenyl]-3H-imidazo[4,5-b]pyridin-6-yl}-carbamic acid isopropyl ester;
(2-Phenyl-3H-imidazo[4,5-b]pyridin-6-yl)-carbamic acid (E)-1-methyl-but-2-enyl ester;
(2-Phenyl-3H-imidazo[4,5-b]pyridin-6-yl)-carbamic acid 1,2-dimethyl-allyl ester;
{2-[4-(2-Diethylamino-ethoxy)-phenyl]-3H-imidazo[4,5-b]pyridin-6-yl}-carbamic acid isopropyl ester;
{2-[3-(2-Methoxy-ethoxy)-phenyl]-3H-imidazo[4,5-b]pyridin-6-yl}-carbamic acid isopropyl ester;
{2-[4-(2-Methoxy-ethoxy)-phenyl]-3H-imidazo[4,5-b]pyridin-6-yl}-carbamic acid isopropyl ester;
[2-(3-Nitro-phenyl)-3H-imidazo[4,5-b]pyridin-6-yl]-carbamic acid isopropyl ester
[2-(4-Morpholin-4-yl-phenyl)-3H-imidazo[4,5-b]pyridin-6-yl]-carbamic acid isopropyl ester;
{2-[4-(4-Methyl-piperazin-1-yl)-phenyl]-3H-imidazo[4,5-b]pyridin-6-yl}-carbamic acid isopropyl ester;
{2-[3-(2-Hydroxy-ethyl)-phenyl]-3H-imidazo[4,5-b]pyridin-6-yl}-carbamic acid isopropyl ester;
[2-(4-Nitro-phenyl)-3H-imidazo[4,5-b]pyridin-6-yl]-carbamic acid isopropyl ester;
[2-(4-Sulfamoyl-phenyl)-3H-imidazo[4,5-b]pyridin-6-yl]-carbamic acid isopropyl ester;
[2-(4-Methylsulfanyl-phenyl)-3H-imidazo[4,5-b]pyridin-6-yl]-carbamic acid isopropyl ester;
[2-(3-Amino-phenyl)-3H-imidazo[4,5-b]pyridin-6-yl]-carbamic acid isopropyl ester;
[2-(4-Amino-phenyl)-3H-imidazo[4,5-b]pyridin-6-yl]-carbamic acid isopropyl ester;
[2-(3-Acetylamino-phenyl)-3H-imidazo[4,5-b]pyridin-6-yl]-carbamic acid isopropyl ester;
[2-(3-Methanesulfonylamino-phenyl)-3H-imidazo[4,5-b]pyridin-6-yl]-carbamic acid isopropyl ester;

[2-(3-Methylsulfinyl-phenyl)-3H-imidazo[4,5-b]pyridin-6-yl]-carbamic acid isopropyl ester;

[2-(3-Methylsulfonyl-phenyl)-3H-imidazo[4,5-b]pyridin-6-yl]-carbamic acid isopropyl ester;

[2-(4-Methanesulfonyl-phenyl)-3H-imidazo[4,5-b]pyridin-6-yl]-carbamic acid isopropyl ester;

[2-(4-Methanesulfinyl-phenyl)-3H-imidazo[4,5-b]pyridin-6-yl]-carbamic acid isopropyl ester;

[2-(3,4-Difluoro-phenyl)-3H-imidazo[4,5-b]pyridin-6-yl]-carbamic acid isopropyl ester;

(2-{4-[Bis-(2-methoxy-ethyl)-amino]-3-fluoro-phenyl}-3H-imidazo[4,5-b]pyridin-6-yl)-carbamic acid isopropyl ester;

3-(6-Isopropoxycarbonylamino-3H-imidazo[4,5-b]pyridin-2-yl)-benzoic acid;

{2-[3-(2-Methoxy-1-methoxymethyl-ethylcarbamoyl)-phenyl]-3H-imidazo[4,5-b]pyridin-6-yl}-carbamic acid isopropyl ester; and {2-[3-(3-Methoxy-propylcarbamoyl)-phenyl]-3H-imidazo[4,5-b]pyridin-6-yl}-carbamic acid isopropyl ester.

Another embodiment of the invention are the compounds according to formula I, wherein $R^1$ is a heteroaryl group optionally substituted one or two times with chlorine, heterocyclyl or —Z-alkyl; and the alkyl groups are optionally substituted one or two times by alkoxy;

Z is a single bond or —NR—;

R is hydrogen;

$R^2$ is alkyl; and

A is ═N—.

Such compounds, for example, may be selected from the group consisting of:

(2-Thiophen-2-yl-3H-imidazo[4,5-b]pyridin-6-yl)-carbamic acid isopropyl ester;

(2-Thiophen-3-yl-3H-imidazo[4,5-b]pyridin-6-yl)-carbamic acid isopropyl ester;

[2-(2-Methyl-pyridin-4-yl)-3H-imidazo[4,5-b]pyridin-6-yl]-carbamic acid isopropyl ester;

[2-(6-Methyl-pyridin-3-yl)-3H-imidazo[4,5-b]pyridin-6-yl]-carbamic acid isopropyl ester;

[2-(1H-Benzoimidazol-5-yl)-3H-imidazo[4,5-b]pyridin-6-yl]-carbamic acid isopropyl ester;

[2-(2-Chloro-pyridin-4-yl)-3H-imidazo[4,5-b]pyridin-6-yl]-carbamic acid isopropyl ester; and {2-[2-(3-Methoxy-propylamino)-pyridin-4-yl]-3H-imidazo[4,5-b]pyridin-6-yl}-carbamic acid isopropyl ester.

Still another embodiment of the invention is a process for the manufacture of the compounds of formula I, wherein (a) the compound of formula II

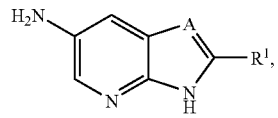

formula II wherein A and $R^1$ have the significance as given in formula I above, is reacted with a compound of formula III

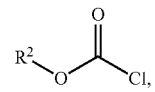

formula III wherein $R^2$ has the significance given above for formula I, to give the respective compound of formula I, (b) said compound of formula I is isolated from the reaction mixture, and (c) if desired, converted into a pharmaceutically acceptable salt.

The derivatives of the general formula I or a pharmaceutically acceptable salt thereof, may be prepared by any process known to be applicable for the preparation of chemically-related compounds by the one skilled in the art. Such processes, when used to prepare the derivatives of formula I, or a pharmaceutically-acceptable salt thereof, are provided as a further feature of the invention and are illustrated by the following representative examples of scheme 1 and 2, in which, unless otherwise stated $R^1$, $R^2$ and A have the significance given herein before for formula I. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Scheme 1
The manufacture of the compounds of formula I varies according to the nature of "A" in formula I. The compounds of the present invention wherein "A" is ═N— can be prepared according to scheme 1, and are named I-A.

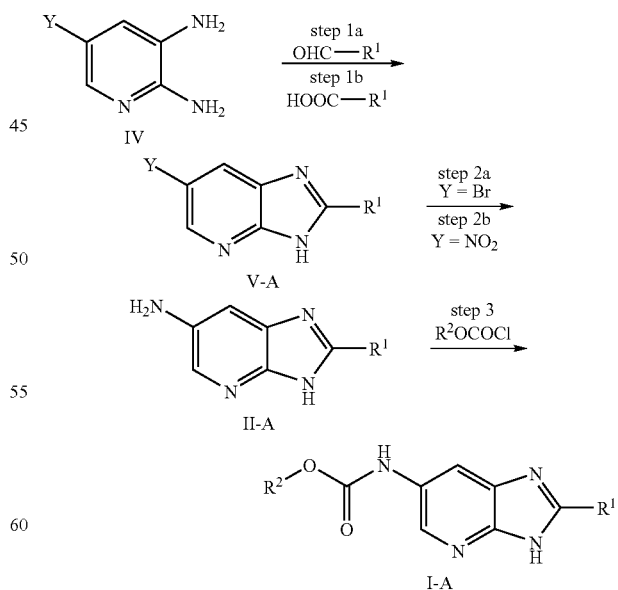

In scheme 1, $R^1$ and $R^2$ have the significance as given above for formula I and Y is bromine (for the route via step 2a) or nitro (for the route via step 2b).

Step 1a: Condensation of an aromatic aldehyde with a 2,3-diamino-pyridine derivative of formula IV can carried out at elevated temperatures from 60 to 200° C. in a suitable solvent like acetonitrile, nitrobenzene, N,N-dimethylformamide (DMF), dimethylsulfoxide (DMSO), xylene, or methoxyethanol, optionally in the presence of an oxidizing agent like oxygen or an iron (III) salt or sulfur, or 2,3-dichloro-5, 6-dicyano-p-benzoquinone (DDQ).

Step 1b: The condensation with an aromatic carboxylic acid, or a suitable derivative thereof, with a 2,3-diamino-pyridine derivative of formula IV can be achieved at temperatures in the range of 100-220° C. with a condensation reagent like polyphosphoric acid, POCl$_3$, or P$_4$O$_{10}$, optionally in mixture with methane sulfonic acid.

Step 2a: In the compounds of formula V-A, wherein Y is bromine, such bromine can be replaced by an amino group by heating in aqueous ammonia in the presence of a catalyst like CuSO$_4$ or CuI. A solubilizing co-solvent like N-methylpyrrolidone (NMP) or dimethyl acetamide can be added, and the reaction is carried out at temperatures of 100-180° C. in a closed vessel.

Alternatively, the amino functionality may be introduced in protected form as a tert.-butoxycarbonylamino substituent via coupling under standard Hartwig/Buchwald conditions (for example, with a base like sodium tert. butoxide and a palladium catalyst like Pd$_2$(dba)$_3$ and a phosphine ligand like tri-tert. butyl phosphane).

Step 2b: For the compounds of formula V-A, wherein Y is nitro, the reduction of the nitro group is accomplished by standard conditions such as heterogeneous hydrogenation with Pd on charcoal as the catalyst, in solvents like methanol, ethanol, tetrahydrofuran (THF), or ethyl acetate, at room temperature or up to 80° C.; or by homogeneous hydrogenation with a Pd catalyst and triethyl ammonium formate in a solvent like methanol at reflux conditions. The reduction can also be carried out with base metals like iron or tin in acidic media like acetic acid or aqueous HCl, from room temperature to 120° C. Another suitable reductant would be ammonium sulfide in water or methanol, or tin (II) chloride in DMF.

Step 3: Acylation of the amino moiety on the compounds of formula II-A can be done with an appropriate chloroformate in an inert solvent like dichloromethane, toluene, tetrahydrofuran (THF), N-methylpyrrolidone (NMP), or dimethyl acetamide, or pyridine, optionally in the presence of a base like pyridine, triethyl amine, or di-isopropyl ethyl amine. Suitable temperatures are in the range of −20° C. to 100° C.

If an excess of chloroformate is used, simultaneous acylation on the heterocyclic core can occur, e.g. on N-1 or N-3. Such a bis-acylated intermediate can be cleaved easily to the desired mono-acylated compound by subsequent treatment with ammonia in water or methanol at room temperature.

Scheme 2
The manufacture of the compounds of formula I varies according to the nature of "A" in formula I. The compounds of the present invention wherein "A" is ≡C— can be prepared according to scheme 2, and are named I-B

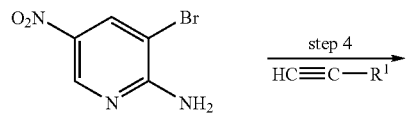

In scheme 2, R$^1$ and R$^2$ have the significance as given above for formula I.

Step 4: An ethynyl-arene can be coupled with 3-bromo-5-nitro-pyridin-2-ylamine under standard conditions of the so called Sonogashira reaction, with a copper catalyst like CuI or CuCl, and a palladium catalyst like PdCl$_2$(PPh$_3$)$_2$ or PdCl$_2$(PhCN)$_2$/PtBu$_3$, and a base like triethyl amine or di-isopropyl amine, in an inert solvent like tetrahydrofuran (THF), dioxane, N,N-dimethylformamide (DMF), or acetonitrile. The reaction proceeds at room temperature or higher, up to 160° C.

Alternatively, the ethynyl-arene may first be converted into a more reactive alkynyl-Zn or -Sn derivative by procedures known in the art: the ethynyl-arene is deprotonated with a strong base like butyl lithium to form an alkynyl-Li intermediate which is reacted with ZnCl$_2$ or Bu$_3$SnCl to yield the desired zinc or tin intermediate. These may subsequently be coupled to the bromopyridine under standard cross coupling conditions, for instance by catalysis by a palladium phosphine complex like Pd(PPh$_3$)$_4$ or PdCl$_2$(PPh$_3$)$_2$ or Pd$_2$(dba)$_3$/PtBu$_3$ in solvents like dimethyl acetamide, THF, or toluene.

Step 5: Cyclisation of the alkyne intermediate to form a pyrrole ring can be achieved by treatment with a base like potassium tert. butoxide, potassium hydride, or sodium ethoxide in an inert solvent like NMP, THF, or DMF, or ethanol, at temperatures in the range from room temperature to reflux. Alternatively, the base can be replaced by a catalyst like CuI.

Step 6 and Step 7: These step are analogous to Step 2b and Step 3 under scheme 1 above.

Certain substituents on the group R$^1$ may not be inert to the conditions of the synthesis sequences described above and may require protection by standard protecting groups known in the art. For instance, an amino or hydroxyl group may be protected as a tert.-butoxycarbonyl derivative. Alternatively, some substituents may be derived from others at the end of the reaction sequence. For instance, a compound of formula I may be synthesized bearing a nitro- or an ethoxycarbonyl or an alkylsulfanyl substituent on the group R$^1$, which substituents are finally converted to an amino-, acylamino-, or alkylsulfonylamino substituent, or to a carboxamide substituent, or to an alkylsulfinyl or alkylsulfonyl substituent by standard procedures.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Stahl, P. H., and Wermuth, G., (editors), Handbook of Pharmaceutical Salts, Verlag Helvetica Chimica Acta (VHCA), Zürich (2002) or Bastin, R. J., et al., Organic Proc. Res. Dev. 4 (2000) 427-435.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

An embodiment of the invention is a medicament containing one or more compounds according to formula I as active ingredients together with pharmaceutically acceptable adjuvants.

Another embodiment of the invention is said medicament for the treatment of diseases mediated by an inappropriate activation of src family tyrosine kinases.

Another embodiment of the invention is said medicament for the treatment of inflammatory-, immunological-, CNS disorders or bone diseases.

Another embodiment of the invention is said medicament for the treatment of cancer.

Another embodiment of the invention is the use of one or more compounds according to formula I for the manufacture of medicaments for the treatment of diseases mediated by an inappropriate activation of src family tyrosine kinases.

Another embodiment of the invention is the use of one or more compounds according to formula I for the manufacture of medicaments for the treatment of cancer.

Another embodiment of the invention is the use of one or more compounds according to formula I for the manufacture of medicaments for the treatment of inflammatory-, immunological-, CNS disorders or bone diseases.

Another embodiment of the invention is the use of one or more compounds according to formula I as src family tyrosine kinase inhibitors.

Another embodiment of the invention is the use of one or more compounds according to formula I as cell signaling-regulating and anti-proliferating agents.

Another embodiment of the invention is the use of one or more compounds according to formula I for the treatment of inflammatory-, immunological-, CNS disorders or bone diseases.

Another embodiment of the invention is the use of one or more compounds of formula I according to formula I for the treatment of cancer.

A pharmaceutical preparation was obtained e.g. by using the following procedure:

1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 µm. The suspensions are suitable for oral applications and were used in the in vivo pharmacokinetic testings described below.

Pharmacological Activity:

The activity of the compounds according to this invention as inhibitors for the src-family tyrosine kinases was shown by using the following assay.

| | SRC-Inhibitor-Assay Parameters: |
|---|---|
| Reaction mixture: | |
| ATP | 5 µM |
| Peptide (Ro + Ja133-Ro): | 10 µM |
| Ja133-Ro | 196 nM |
| Ro | 9.8 µM |
| PT66 | 230 ng/ml |
| Assay buffer: | 4 mM MgCl2 |
| | 2 mM TCEP |
| | 50 mM HEPES |
| | 0.1% Tween 20 |
| | pH 7.3 |
| Enzyme: | 2.5 U/ml |
| Inhibitor: | max. 25 µM |
| | min. 0.42 nM |
| | Material: |
| Eu-labelled phosphotyrosine antibody: | for Lck Cisbio Mab PT66-K, |
| | for Src EG&G Wallac PT66 Eu-W1024 |
| | (all commercially available). |
| Peptides: | |
| Ro: | $NH_2$-A-E-E-E-I-Y-G-E-F-E-A-K-K-K-K-$CONH_2$ (SEQ ID NO: 1), and |
| Ja133-Ro: | Ja133-G-Aminocaprylic acid-A-E-E-E-I-Y-G-E-F-E-A-K-K-K-K-$CONH_2$ (SEQ ID NO: 1), wherein Ja133 is LightCycler-Red 640-N-hydroxy succinimide ester; |
| | whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of amino acids each protected by temporary piperidine labile Fmoc- and permanent acid labile tert-Bu-, BOC- and O-tert-Bu-groups depending on the side chain function. The substrate sequence AEEEIYGEFEAKKKK (SEQ ID NO: 1) was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0]. |
| Enzymes: | Upstate Lck ($p56^{lck}$, active), Upstate Src ($p60^{c-src}$, partially purified) were purchased from UBI, Upstate Biotech, Inc.. |
| Time-resolved Fluorescence Assay: | Reader: Perkin Elmer, Wallac Viktor 1420-040 multilabel counter; Liquid handling system: Beckman Coulter, Biomek 2000. |

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK))

| Example-No. | IC50 src [µM] | IC50 lck [µM] |
|---|---|---|
| 6-1 | 0.039 | 0.791 |
| 2-4 | 0.185 | 1.343 |
| 1-11 | 0.228 | 5.0-10.0 |
| 1-1, 1-2, 1-9, 1-10, 1-13, 1-14, 1-15, 1-16, 1-17, 1-22, 2-1, 2-3, 2-5, 2-8, 2-9, 3-1, 3-2, 3-4, 3-7, 5-1, 5-2, 7-1, 8-1, 8-2, 8-4, 9-1, 9-3, 9-4, 9-5, 9-8, 9-17, 9-19, 9-20, 9-23, 9-25, 9-2810-1, 10-2, 11-2, 11-3, 12-1 | 0.010-0.500 | 0.100-9.000 |
| 1-10, 1-12, 1-19, 3-2, 9-3, 11-1 | 0.500-1.500 | 2.000-9.000 |

The following examples and references are provided to aid the understanding of the present invention, the true scope of which is set forth in the appended claims. It is understood that modifications can be made in the procedures set forth without departing from the spirit of the invention.

EXPERIMENTAL PROCEDURES

Examples

Starting Materials 5-bromo-2,3-diaminopyridine was purchased from Aldrich.

2,3-diamino-5-nitropyridine was prepared as described in Cai, S. X., et al, J. Med. Chem. 40 (1997) 3679-3686.

Chloroformates were commercially available, or prepared as follows:

3-Buten-2-yl chloroformate

To 83 mg 3-buten-2-ol (1.15 mmol) in 2 ml dichloromethane were added at 0° C. 136 mg triphosgene. 91 mg pyridine were added dropwise and stirring was continued for 1 hr at room temperature. The resulting solution was used directly for the next step.

The substituted benzaldehydes used are known in the art and prepared by literature procedures, for instances as described for 4-morpholino-benzaldehyde in Magdolen, P., et al, Tetrahedron 5 (2001) 4781-4785, or as described below:

4-(2-Diethylamino-ethoxy)-benzaldehyde 4.82 g potassium hydroxide were dissolved in 70 ml ethanol and treated with 8.46 g (2-Chloro-ethyl)-diethyl-amine hydrochloride. The mixture was stirred until everything was dissolved, then 5.0 g benzaldehyde were added and refluxed for 16 hrs. The mixture was diluted with water and extracted with ethyl acetate, and the organic phases washed several times with caustic soda. After drying and evaporation of the solvent the crude product was used without further purification.

Yield 3.90 g

3-[2-(Tetrahydro-pyran-2-yloxy)-ethyl]-benzaldehyde 2.14 g (7.52 mmol) 2-[2-(3-Bromo-phenyl)-ethoxy]-tetrahydro-pyran in 9 ml dry THF were cooled to −78° C. and treated dropwise with 9.87 ml of 1.6M solution of butyl lithium in hexane (15.79 mmol). After stirring for 30 min, 2.31 g (31.58 mmol) N,N-dimethylformamide were added dropwise and stirring was continued for another 15 min at −78° C. The mixture was slowly warmed to room temperature and stirred for and another 60 min. Water and dichloromethane were added, the organic phase separated, and the aqueous phase extracted several times with dichloromethane. The combined organic phases were dried, evaporated and the residue purified by chromatography on silica in ethyl acetate heptane mixtures.

Yield 1.66 g of the title compound as a pale yellow oil.

N-(3-Formyl-phenyl)-3-methoxy-propionamide 0.76 g (7.31 mmol) 3-methoxypropionic acid in 10 ml dry DMF were treated with 1.25 g (7.71 mmol) 1,1'-carbonyldiimidazole and stirred for 1 hr at room temperature. 1.00 g 3-aminobenzylalcohol were added and stirring was continued over night. The solvent was removed and the residue chromatographed on silica in ethyl acetate, yielding 1.26 g N-(3-Hydroxymethyl-phenyl)-3-methoxy-propionamide.

The above 1.26 g N-(3-Hydroxymethyl-phenyl)-3-methoxy-propionamide were dissolved in 50 ml acetone, 12.60 g manganese dioxide were added and the mixture stirred at room temperature over night. The mixture was filtered and the filtrate evaporated and further purified by chromatography on silica in ethyl acetate/heptane mixtures.

Yield 0.77 g of the title compound as a colourless oil.

Substituted phenyl-acetylenes were prepared by acylation of 3- or 4-amino-phenylacetylene by literature procedures, as described in U.S. Pat. No. 4,162,265A, or by alkylation of 3- or 4-hydroxyphenylacetylene by literature procedures. For instance, 3-(2-methoxyethoxy)phenylacetylene 3-Hydroxyphenylacetylene (237 mg, 2 mmol) was heated with 2-bromoethylmethylether (0.23 mL, 2.4 mmol) and potassium carbonate (322 mg, 2.4 mmol) in acetone (5 mL) to 110° C. in a microwave oven (CEM Discover) for 45 minutes. Water (1 mL) was added to the mixture and the whole was extracted with dichloromethane (2×25 mL). The combined organics were dried over $MgSO_4$, filtered and concentrated in vacuo to afford a brown oil. The oil was purified by column chromatography ($SiO_2$, dichloromethane) to afford 3-(2-methoxyethoxy)phenylacetylene as a colourless oil (247 mg, 70% yield).

$^1$H-NMR (400 MHz; $CDCl_3$): δ=7.23 (1H, dd, J 8.8, 8.0), 7.08 (1H, dt, J 7.6, 1.2), 7.04 (1H, dd, J 1.48, 2.7), 6.94 (1H, ddd, J 1.0, 2.6, 8.3), 4.11 (2H, t, J 4.6), 3.74 (2H, t, J 4.6), 3.45 (3H, s), 3.05 (1H, s).

Alternatively, 4-(2-methoxyethoxy)phenylacetylene was prepared from the corresponding iodobenzene and trimethylsilylacetylene by Sonogashira coupling, as described for 4-methoxyphenylacetylene in Tsuji, M., J. Org. Chem. 68 (2003) 9589-9597-supporting information S.1-36-http://pubs.acs.org/subscribe/journals/joceah/suppinfo/jo035090f/jo035090fsi20030918_025110.pdf.

3-(acetylamino)phenylacetylene

Acetic anhydride (13.8 mL, 144 mmol) was added dropwise to a solution of 3-ethynylaniline (14.0 g, 120 mmol) and 4-(Dimethylamino-)pyridine (DMAP) (1.5 g, 12 mmol) in tetrahydrofuran (300 mL). The mixture was stirred at room temperature for 2 hours, water (100 mL) was added to the mixture and the whole was extracted with dichloromethane (2×250 mL). The combined organics was washed with 10% citric acid (100 mL) followed by saturated sodium bicarbonate solution (100 mL), dried over $MgSO_4$, filtered and concentrated in vacuo to afford 3-(acetylamino)phenylacetylene as a yellow solid (18.3 g, 96%).

$^1$H-NMR (400 MHz; $CDCl_3$): δ=7.62 (1H, s), 7.53 (1H, d, J 7.7), 7.41 (1H, br.s), 7.28-7.22 (2H, m), 3.06 (1H, s), 2.17 (3H, s).

6-Morpholin-4-yl-nicotinic acid 3.00 g 6-chloronicotinic acid in 24 ml dry acetonitrile were mixed with 16.6 ml morpholine and heated to reflux for 48 hrs. The mixture was evaporated under vacuum and the residue dissolved in water. The crude product was precipitated by addition of 10% aqueous acetic acid, isolated by filtration and washed with water and methanol to give 1.83 g of the title compound.

Final Products

Example 1-1

(2-Phenyl-3H-imidazo[4,5-b]pyridin-6-yl)-carbamic acid 1-methyl-allyl ester a) 6-Nitro-2-phenyl-3H-imidazo[4,5-b]pyridine 14.05 g 2,3-diamino-5-nitropyridine and 9.68 g benzaldehyde in 250 ml nitrobenzene were heated to 140-150° C. for 15 hrs. The solvent is removed by vacuum distillation and the residue is dispersed in ethyl acetate, filtered, and the filter residue washed thoroughly with ethyl acetate.

Yield 16.0 g b) 2-phenyl-3H-imidazo[4,5-b]pyridin-6-ylamine 12.0 g 6-nitro-2-phenyl-3H-imidazo[4,5-b]pyridine were dissolved in 1 l acetic acid. 18 g iron powder were added and the mixture heated to 80° C. with stirring. After 2 hrs the mixture was cooled to room temperature and filtered over Celite. The celite pad was washed with methanol and the combined filtrates were evaporated. The residue was dissolved methanol/dichloromethane 1:1 and filtered over silica. The filtrate was concentrated to a volume of 100 ml, the resulting precipitate collected by filtration and washed with methanol.

Yield 7.68 g

(2-Phenyl-3H-imidazo[4,5-b]pyridin-6-yl)-carbamic acid 1-methyl-allyl ester 80 mg 2-phenyl-3H-imidazo[4,5-b]pyridin-6-ylamine (0.38 mmol,) in 3 ml dry pyridine were treated with a solution of 3-buten-2-yl chloroformate in dichloromethane. The mixture was stirred at room temperature over night, diluted with 1 ml water and stirred for another hr. The solvents were evaporated and the residue was dispersed in water with sonication, filtered, and the filter residue washed thoroughly with water and ether.

Yield 11 mg.

$^1$H-NMR (400 MHz, $D_6$-DMSO): δ=13.05 (broad s, 1H); 9.67 (broad s, 1H); 8.15 (s, 1H); 7.96 (d, 3H); 7.37-7.28 (m, 3H); 5.80-5.71 (m, 1H); 5.10 (m, 2H); 4.96 (d, 1H); 1.13 (d, 3H).

The following examples were obtained in analogous fashion as described for example 1-1:

| Example-No. | Systematic Name | $^1$H-NMR | Melting point (° C.) |
|---|---|---|---|
| 1-2 | (2-Phenyl-1H-imidazo[4,5-b]pyridin-6-yl)-carbamic acid isopropyl ester | (400 MHz, $D_6$-DMSO): δ = 13.46 (s) and 13.00 (s, together 1H); 9.82 (broad s) and 9.69 (broad s, together 1H); 8.36 (d, 1H); 8.38-8.15 (m, 3H); 7.60-7.52 (m, 3H); 4.94 (hep, 1H); 1.28 (d, 6H). | |
| 1-3 | (2-Phenyl-3H-imidazo[4,5-b]pyridin-6-yl)-carbamic acid cyclohexyl ester | (400 MHz, $D_6$-DMSO): δ = 13.45 (s) and 12.98 (s, together 1H); 9.84 (broad s) and 9.71 (broad s, together 1H); 8.37 (s, 1H); 8.18 (broad s, 3H); 7.57-7.51 (m, 3H); 4.68 (m, 1H); 1.93 (m, 2H); 1.74 (m, 2H); 1.53-1.20 (m, 6H). | |
| 1-4 | (2-Phenyl-3H-imidazo[4,5-b]pyridin-6-yl)-carbamic acid isobutyl ester | (400 MHz, $D_6$-DMSO): δ = 13.46 (s) and 13.00 (s, together 1H); 9.90 (broad s) and 9.78 (broad s, together 1H); 8.37 (d, 1H); 8.23-8.15 (m, 3H); 7.60-7.52 (m, 3H); 3.92 (d, 2H); 1.96 (m, 1H); 0.96 (d, 6H). | |

-continued

| Example-No. | Systematic Name | ¹H-NMR | Melting point (° C.) |
|---|---|---|---|
| 1-5 | (2-Phenyl-3H-imidazo[4,5-b]pyridin-6-yl)-carbamic acid allyl ester | (400 MHz, $D_6$-DMSO) 13.40 (broad s) and 13.05 (broad s, together 1H); 9.93 (broad s, 1H); 8.37 (s, 1H); 8.18 (s, 3H); 7.59-7.48 (m, 3H); 6.07-5.97 (m, 1H); 5.39 (d, 1H); 5.26 (d, 1H); 4.66 (d, 2H). | |
| 1-6 | (2-Phenyl-3H-imidazo[4,5-b]pyridin-6-yl)-carbamic acid tert-butyl ester | (400 MHz, $D_6$-DMSO) 13.45 (broad s) and 12.95 (broad s, together 1H); 9.61 (broad s) and 9.46 (broad s, together 1H); 8.37 (s, 1H); 8.15 (m, 3H); 7.55 (m, 3H); 1.51 (s, 9H). | |
| 1-7 | (2-Phenyl-3H-imidazo[4,5-b]pyridin-6-yl)-carbamic acid cyclopentyl ester | (400 MHz, $D_6$-DMSO): δ = 13.42 (s) and 13.00 (s, together 1H); 9.80 (broad s) and 9.68 (broad s, together 1H); 8.36 (s, 1H); 8.18 (s, 3H); 7.57-7.52 (m, 3H); 5.14 (m, 1H); 1.89 (m, 2H); 1.71 (m, 4H); 1.61 (m, 2H). | |
| 1-8 | (2-Phenyl-3H-imidazo[4,5-b]pyridin-6-yl)-carbamic acid ethyl ester | (400 MHz, $D_6$-DMSO): δ = 13.20 (broad s, 1H); 9.82 (broad s, 1H); 8.36 (s, 1H); 8.18 (broad s, 3H); 7.58-7.55 (m, 3H); 4.17 (broad d, 2H); 1.28 (broad s, 3H). | |
| 1-9 | (2-Phenyl-3H-imidazo[4,5-b]pyridin-6-yl)-carbamic acid sec-butyl ester | (400 MHz, $D_6$-DMSO): δ = 13.46 (broad s) and 13.00 (broad s, together 1H); 9.83 (broad s) and 9.70 (broad s, together 1H); 8.37 (s, 1H); 8.19 (m, 3H); 7.58-7.50 (m, 3H); 4.78 (hex, 1H); 1.61 (m, 2H); 1.26 (d, 3H); 0.94 (t, 3H). | |
| 1-10 | (2-Phenyl-3H-imidazo[4,5-b]pyridin-6-yl)-carbamic acid 1-ethyl-propyl ester | (400 MHz, $D_6$-DMSO): δ = 13.40 (broad s, 1H); 9.81 (broad s, 1H); 8.39 (s, 1H); 8.19 (m, 3H); 7.59-7.51 (m, 3H); 4.68 (m, 1H); 1.60 (m, 4H); 0.92 (t, 6H). | |
| 1-11 | (2-Phenyl-3H-imidazo[4,5-b]pyridin-6-yl)-carbamic acid 2,2,2-trifluoro-1-methyl-ethyl ester | (400 MHz, $D_6$-DMSO): δ = 10.27 (broad s, 1H); 8.42 (s, 1H); 8.20 (m, 3H); 7.60-7.53 (m, 3H); 5.47 (m, 1H); 1.46 (d, 3H). | |
| 1-12 | (2-Phenyl-3H-imidazo[4,5-b]pyridin-6-yl)-carbamic acid 2,2-dimethyl-propyl ester | (400 MHz, $D_6$-DMSO): δ = 13.30 (broad s, 1H); 9.80 (broad s, 1H); 8.39 (s, 1H); 8.19 (m, 3H); 7.58-7.54 (m, 3H); 3.85 (s, 2H); 0.98 (s, 9H). | |
| 1-13 | (2-Phenyl-3H-imidazo[4,5-b]pyridin-6-yl)-carbamic acid 1-phenyl-ethyl ester | (400 MHz, $D_6$-DMSO): δ = 13.25 (broad s, 1H); 9.95 (broad s, 1H); 8.36 (s, 1H); 8.18 (m, 3H); 7.58-7.51 (m, 3H); 7.51-7.42 (m, 4H; 7.32 (t, 1H); 5.86 (q, 1H); 1.57 (d, 3H). | |
| 1-14 | (2-Phenyl-1H-imidazo[4,5-b]pyridin-6-yl)-carbamic acid propyl ester | | |
| 1-15 | (2-Phenyl-3H-imidazo[4,5-b]pyridin-6-yl)-carbamic acid 1-methyl-prop-2-ynyl ester | (400 MHz, $D_6$-DMSO): δ = 13.49 (broad s) and 13.25 (broad s, together 1H); 10.09 (broad s) and 9.96 (broad s, together 1H); 8.37 (d, 1H); 8.23-8.17 (m, 3H); 7.56 (m, 3H); 5.44 (q, 1H); 3.59 (s, 1H); 1.52 (d, 3H). | |

-continued

| Example-No. | Systematic Name | ¹H-NMR | Melting point (° C.) |
|---|---|---|---|
| 1-16 | (2-Phenyl-3H-imidazo[4,5-b]pyridin-6-yl)-carbamic acid 1-methyl-but-2-ynyl ester | (400 MHz, $D_6$-DMSO): δ = 13.48 (broad s) and 13.05 (broad s, together 1H); 10.03 (broad s) and 9.90 (broad s, together 1H); 8.36 (d, 1H); 8.22 (d, 1H); 8.17 (m, 2H); 7.60-7.51 (m, 3H); 5.42 (q, 1H); 1.85 (s, 3H); 1.49 (d, 3H). | |
| 1-17 | (2-Phenyl-3H-imidazo[4,5-b]pyridin-6-yl)-carbamic acid cyclobutyl ester | (400 MHz, $D_6$-DMSO): δ = 13.25 (broad s, 1H); 9.85 (broad s, 1H); 8.36 (s, 1H); 8.18 (d, 3H); 7.55 (m, 3H); 4.99 (m, 1H); 2.31 (m, 2H); 2.08 (m, 2H); 1.77 (q, 1H); 1.62 (m, 1H). | |
| 1-18 | (2-Phenyl-3H-imidazo[4,5-b]pyridin-6-yl)-carbamic acid 1,3-dimethyl-butyl ester | (400 MHz, $D_6$-DMSO): δ = 9.82 (broad s) and 9.69 (broad s, together 1H); 8.37 (d, 1H); 8.18 (m, 3H); 7.56 (m, 3H); 4.93 (m, 1H); 1.80-1.51 (m, 4H); 1.37 (m, 1H); 1.26 (d, 3H); 0.92 (d, 6H). | |
| 1-19 | (2-Phenyl-3H-imidazo[4,5-b]pyridin-6-yl)-carbamic acid 1,2-dimethyl-propyl ester | (400 MHz, $D_6$-DMSO): δ = 13.44 (broad s) and 13.02 (broad s, together 1H); 9.77 (broad s, 1H); 8.38 (s, 1H); 8.18 (s, 3H); 7.54 (m, 3H); 4.67 (m, 1H); 1.95 (m, 1H); 1.21 (d, 3H); 0.95 (d, 6H). | |
| 1-20 | {2-[3-(3-Methoxy-propionylamino)-phenyl]-3H-imidazo[4,5-b]pyridin-6-yl}-carbamic acid isopropyl ester | (400 MHz, $D_6$-DMSO): δ = 10.16 (s, 1H); 9.83 (broad s) and 9.70 (broad s, together 1H); 8.51 (s, 1H); 8.36 (s, 1H); 8.18 (s, 1H); 7.81 (s, 1H); 7.69 (s, 1H); 7.48 (t, 1H); 4.94 (m, 1H); 3.66 (t, 2H); 3.27 (s, 3H); 2.60 (t, 2H); 1.29 (d, 6H). | | tetrahydrofuran (THF) fff

Example 1-21

(2-Phenyl-3H-imidazo[4,5-b]pyridin-6-yl)-carbamic acid (E)-1-methyl-but-2-enyl ester 32 mg 3-penten-2-ol (0.38 mmol,) in 1 ml dry dichloromethane were treated at 0° C. with 62 mg 1,1'-carbonyldiimidazole. The mixture was stirred at 0° C. for 2 hrs. 80 mg 2-phenyl-3H-imidazo[4,5-b]pyridin-6-ylamine (0.38 mmol,) in 0.5 ml N-methylpyrrolidone (NMP) were added and the mixture stirred over night at room temperature. 1 ml water was added, the precipitate filtered, and the filter residue washed thoroughly with water and ether and further purified by chromatography.

Yield 3 mg.

¹H-NMR (400 MHz, $D_6$-DMSO): δ=13.08 (broad s, 1H); 9.81 (broad s, 1H); 8.35 (s, 1H); 8.18 (d, 3H); 7.59-7.50 (m, 3H); 5.77 (m, 1H); 5.59 (dd, 1H); 5.27 (m, 1H); 1.67 (d, 3H); 1.34 (d, 3H).

The following example was obtained in analogous fashion as described for example 1-21:

Example 1-22

(2-Phenyl-3H-imidazo[4,5-b]pyridin-6-yl)-carbamic acid 1,2-dimethyl-allyl ester

¹H-NMR (400 MHz, $D_6$-DMSO): δ=13.45 (broad s) and 13.00 (broad s, together 1H); 9.93 (broad s) and 9.80 (broad s, together 1H); 8.37 (d, 1H); 8.21 (d) and 8.16 (d, together 3H); 7.60-7.51 (m, 3H); 5.23 (q, 1H); 5.03 (s, 1H); 4.90 (s, 1H); 1.78 (s, 3H); 1.36 (d, 3H).

Example 2-1

{2-[4-(2-Diethylamino-ethoxy)-phenyl]-3H-imidazo[4,5-b]pyridin-6-yl}-carbamic acid isopropyl ester a) {2-[4-(6-Bromo-3H-imidazo[4,5-b]pyridin-2-yl)-phenoxy]-ethyl}-diethyl-amine 3.31 g 5-bromo-2,3-diaminopyridine and 3.90 g 4-(2-diethylamino-ethoxy)benzaldehyde in 120 ml nitrobenzene were heated to 140-150° C. for 24 hrs. The solvent was removed by vacuum distillation. The residue was dispersed in ethyl acetate and the crude product was isolated by filtration and washed thoroughly with more ethyl acetate.

Yield 1.45 g b) 2-[4-(2-Diethylamino-ethoxy)-phenyl]-3H-imidazo[4,5-b]pyridin-6-ylamine To 250 mg of the product from example 2-1a) in 1 ml N-methylpyrrolidone (NMP) were added 32 mg copper sulfate pentahydrate and 3.1 ml conc. ammonia. The mixture was heated in a capped glass vial in a microwave oven at 151° C. and 18 bar for 5 hrs. After cooling, the mixture was diluted with methanol, filtered, and evaporated. The residue was transferred in water onto a short column of RP (C-18) silica and eluted with water. Evaporation of the eluent gave 105 mg of the title product.

{2-[4-(2-Diethylamino-ethoxy)-phenyl]-3H-imidazo[4,5-b]pyridin-6-yl}-carbamic acid isopropyl ester 100 mg of the product of example 2-1b) in 4 ml dry pyridine were treated at room temperature with 0.92 ml of a 1M solution of isopropyl chloroformate in toluene. Stirring was continued for 15 hrs. The mixture was evaporated, re-dissolved in 3 ml methanol and 1 ml of conc. ammonia were added. After stirring for 1 hr at room temperature, the mixture was again evaporated and the residue purified by preparative HPLC-MS (MeOH/H$_2$O/HOAc eluent).

Yield 41 mg of the acetate salt of the title product.

$^1$H-NMR (500 MHz, D$_6$-DMSO): δ=13.00 (broad s, 1H); 9.66 (broad s, 1H); 8.32 (s, 1H); 8.11 (broad d, 3H); 7.11 (broad d, 2H); 4.94 (m, 1H); 4.11 (t, 2H); 2.82 (t, 2H); 2.58 (m, not separated from DMSO); 1.29 (d, 6H); 0.99 (t, 6H).

The following examples were obtained in analogous fashion as described for example 2-1:

| Example-No. | Systematic Name | $^1$H-NMR | Melting point (° C.) |
|---|---|---|---|
| 2-2 | {2-[3-(2-Methoxy-ethoxy)-phenyl]-3H-imidazo[4,5-b]pyridin-6-yl}-carbamic acid isopropyl ester | (400 MHz, D$_6$-DMSO): δ = 13.42 (broad s) and 12.97 (broad s, together 1H); 9.82 (broad s) and 9.68 (broad s, together 1H); 8.37 (s, 1H); 8.18 (s, 1H); 7.79 (broad s) and 7.74 (broad s, together 2H); 7.47 (m, 1H); 7.11 (m, 1H); 4.94 (m, 1H); 4.21 (broad s, 2H); 3.72 (broad s; 2H); 3.32 (s, not separated from H2O); 1.29 (d, 6H). | |
| 2-3 | {2-[4-(2-Methoxy-ethoxy)-phenyl]-3H-imidazo[4,5-b]pyridin-6-yl}-carbamic acid isopropyl ester | (400 MHz, D$_6$-DMSO): δ = 9.80 (broad s) and 9.65 (broad s, together 1H); 8.32 (s, 1H); 8.13 (m, 3H); 7.14 (m, 2H); 4.94 (m, 1H); 4.20 (broad s, 2H); 3.70 (broad s; 2H); 3.32 (s, not separated from H2O); 1.28 (d, 6H). | |
| 2-4 | [2-(3-Nitro-phenyl)-3H-imidazo[4,5-b]pyridin-6-yl]-carbamic acid isopropyl ester | (400 MHz, D$_6$-DMSO): δ = 13.48 (broad s, 1H); 9.74 (broad s, 1H); 8.94 (s, 1H); 8.53 (d, 1H); 8.34 (s, 1H); 8.28 (m, 1H); 8.16 (s, 1H); 7.80 (t, 1H); 4.86 (m, 1H); 1.21 (d, 6H). | |
| 2-5 | [2-(4-Morpholin-4-yl-phenyl)-3H-imidazo[4,5-b]pyridin-6-yl]-carbamic acid isopropyl ester | (400 MHz, D$_6$-DMSO): δ = 13.14 (broad s) and 12.70 (broad s, together 1H); 9.74 (broad s) and 9.62 (broad s, together 1H); 8.29 (s, 1H); 8.06 (m, 3H); 7.09 (d, 2H); 4.93 (m, 1H); 3.76 (broad s, 4H); 3.27 (broad s; 4H); 1.28 (d, 6H). | |
| 2-6 | (2-Thiophen-2-yl-3H-imidazo[4,5-b]pyridin-6-yl)-carbamic acid isopropyl ester | (400 MHz, D$_6$-DMSO): δ = 13.50 (broad s) and 13.00 (broad s, together 1H); 9.81 (broad s) and 9.67 (broad s, together 1H); 8.33 (broad d, 1H); 8.12 (broad d, 1H); 7.91 (d) and 7.84 (d, together 1H); 7.78 (m, 1H); 7.26 (m, 1H); 4.93 (m, 1H); 1.28 (d, 6H). | |
| 2-7 | (2-Thiophen-3-yl-3H-imidazo[4,5-b]pyridin-6-yl)-carbamic acid isopropyl ester | | m.p. 342° C. (decomposition) |
| 2-8 | {2-[4-(4-Methyl-piperazin-1-yl)-phenyl]-3H-imidazo[4,5-b]pyridin-6-yl}-carbamic acid isopropyl ester | (400 MHz, CD$_3$OD): δ = 8.26 (s, 2H); 8.03 (d, 2H); 7.13 (d, 2H); 5.02 (m, 1H); 3.45 (broad s, 4H); 2.86 (broad s, 4H); 2.54 (s, 3H); 1.34 (d, 6H). | |

Example 2-9

{2-[3-(2-Hydroxy-ethyl)-phenyl]-3H-imidazo[4,5-b]pyridin-6-yl}-carbamic acid isopropyl ester a) 2-{3-[2-(Tetrahydro-pyran-2-yloxy)-ethyl]-phenyl}-3H-imidazo[4,5-b]pyridin-6-ylamine was prepared as described for example 2-1 starting from 5-bromo-2,3-diaminopyridine and 3-[2-(Tetrahydro-pyran-2-yloxy)-ethyl]-benzaldehyde.

b) {2-[3-(2-Hydroxy-ethyl)-phenyl]-3H-imidazo[4,5-b]pyridin-6-yl}-carbamic acid isopropyl ester 210 mg (0.62 mmol) 2-{3-[2-(Tetrahydro-pyran-2-yloxy)-ethyl]-phenyl}-3H-imidazo[4,5-b]pyridin-6-ylamine were dissolved in 2 ml dry N-methylpyrrolidone (NMP) and cooled to 0° C. 0.683 ml of a 1M solution of iso-propyl chloroformate in toluene (0.683 mmol) were added and stirring was continued for 10 min at 0° C. and for further 3 hrs at room temperature. The solvents were removed under vacuum and the residue taken up in 3 ml methanol and 1 ml conc. aqueous ammonia. The mixture was stirred for 1 hr at room temperature before it was evaporated. The residue was purified by chromatography on silica in ethyl acetate methanol mixtures, yielding 55 mg of the deprotected hydroxyethyl title compound.

$^1$H-NMR (400 MHz, D$_6$-DMSO): δ=13.40 (s) and 12.94 (s, together 1H); 9.81 (broad s) and 9.68 (broad s, together 1H); 8.35 (d, 1H); 8.17 (s, 1H); 8.03-7.96 (m, 2H); 7.46 (q, 1H); 7.38 (d, 1H); 4.94 (m, 1H); 4.71 (m, 1H, exchanges with D2O); 3.69 (m, 2H); 2.83 (m, 2H); 4H); 1.29 (d, 6H).

Example 3-1

[2-(2-Methyl-pyridin-4-yl)-3H-imidazo[4,5-b]pyridin-6-yl]-carbamic acid isopropyl ester a) 6-Bromo-2-(2-methyl-pyridin-4-yl)-3H-imidazo[4,5-b]pyridine 0.30 g 5-bromo-2,3-diaminopyridine and 0.212 g 2-methyl-pyridine-4-carboxylic acid were heated in 3 g polyphosphoric acid at 160° C. with stirring for 16 hrs. The mixture was diluted with water and insoluble components removed by filtration. Water was evaporated from the filtrate and the residue dispersed in pyridine. Again, insoluble components were removed by filtration and the filtrate evaporated. The obtained residue was washed thoroughly with water and dried.

Yield 130 mg.

b) [2-(2-Methyl-pyridin-4-yl)-3H-imidazo[4,5-b]pyridin-6-yl-amine

Obtained from 3-1a) and ammonia analogous to example 2-1b). Purification by chromatography on silica in methanol/dichloromethane mixtures.

[2-(2-Methyl-pyridin-4-yl)-3H-imidazo[4,5-b]pyridin-6-yl]-carbamic acid isopropyl ester Obtained from 3-1b) and isopropyl chloro formate analogous to example 2-1.

$^1$H-NMR (400 MHz, D$_6$-DMSO): δ=13.74 (broad s) and 13.29 (broad s, together 1H); 9.90 (broad s) and 9.75 (broad s, together 1H); 8.64 (t, 1H); 8.43 (s, 1H); 8.24 (s, 1H); 8.02 (s) and 7.96 (s, together 1H); 7.92 (d) and 7.86 (d, together 1H); 4.95 (m, 1H); 2.58 (s, 3H); 1.29 (d, 6H).

The following examples were obtained in analogous fashion as described for example 3-1:

| Example-No. | Systematic Name | $^1$H-NMR |
|---|---|---|
| 3-2 | [2-(6-Methyl-pyridin-3-yl)-3H-imidazo[4,5-b]pyridin-6-yl]-carbamic acid isopropyl ester | (400 MHz, D$_6$-DMSO): δ = 13.58 (s) and 13.10 (s, together 1H); 9.85 (broad s) and 9.70 (broad s, together 1H); 9.24 (s) and 9.19 (s, together 1H); 8.42-8.34 (m, 2H); 8.20 (s, 1H); 7.46 (t, 1H); 4.94 (m, 1H); 2.56 (s, 3H); 1.28 (d, 6H). |
| 3-3 | [2-(3-Methylsulfanyl-phenyl)-3H-imidazo[4,5-b]pyridin-6-yl]-carbamic acid isopropyl ester | (400 MHz, D$_6$-DMSO): δ = 9.83 (broad s) and 9.72 (broad s, together 1H); 8.37 (s, 1H); 8.18 (s, 1H); 8.04 (m, 1H); 7.93 (m, 1H); 7.50 (m, 1H); 7.40 (broad d, 1H); 4.94 (m, 1H); 2.59 (s, 3H); 1.28 (d, 6H). |
| 3-4 | [2-(4-Nitro-phenyl)-3H-imidazo[4,5-b]pyridin-6-yl]-carbamic acid isopropyl ester | (400 MHz, D$_6$-DMSO): δ = 13.35 (broad s, 1H); 9.85 (broad s, 1H); 8.43 (broad s, 5H); 8.26 (s, 1H); 4.94 (m, 1H); 1.29 (d, 6H). |
| 3-5 | [2-(1H-Benzoimidazol-5-yl)-3H-imidazo[4,5-b]pyridin-6-yl]-carbamic acid isopropyl ester | (400 MHz, CD$_3$OD): δ = 8.47 (s, 1H); 8.33 (m, 3H); 8.10 (d, 1H); 7.80 (d, 1H); 5.03 (m, not separated from H2O); 1.35 (d, 6H). |
| 3-6 | [2-(4-Sulfamoyl-phenyl)-3H-imidazo[4,5-b]pyridin-6-yl]-carbamic acid isopropyl ester | (400 MHz, CD$_3$OD): δ = 8.35 (broad s, 2H); 8.20 (d, 2H); 8.02 (d, 2H); 5.02 (m, not separated from H2O); 1.35 (d, 6H). |

-continued

| Example-No. | Systematic Name | ¹H-NMR |
|---|---|---|
| 3-7 | [2-(6-Morpholin-4-yl-pyridin-3-yl)-3H-imidazo[4,5-b]pyridin-6-yl]-carbamic acid isopropyl ester | (400 MHz, $D_6$-DMSO): δ = 9.69 (broad s, 1H); 8.91 (s, 1H); 8.30 (s) and 8.26 (d, together 2H); 8.10 (s, 1H); 7.01 (d, 1H); 4.93 (m, 1H); 3.72 (broad s, 4H); 3.60 (broad s, 4H); 1.28 (d, 6H). |

Example 4-1

[2-(4-Methylsulfanyl-phenyl)-3H-imidazo[4,5-b]pyridin-6-yl]-carbamic acid isopropyl ester a) 2-(4-Methylsulfanyl-phenyl)-6-nitro-3H-imidazo[4,5-b]pyridine 1.0 g 2,3-diamino-5-nitropyridine and 1.125 g 4-methylsulfanylbenzoic acid in 20 ml polyphosphoric acid were heated to 160° C. with stirring for 15 hrs. The mixture was cooled and poured into water. The pH was adjusted to 4-5 by addition of sodium hydroxide and the precipitate collected by filtration. The filtration residue was stirred in 50 ml pyridine at 60° C., cooled and insoluble components removed by filtration. The filtrate was evaporated and the residue used without further purification in the next steps.

Yield 0.656 g of 30% purity b) 2-(4-Methylsulfanyl-phenyl)-3H-imidazo[4,5-b]pyridin-6-yl-amine 0.656 g of the nitro compound from example 4-1a) and 0.326 g of powdered tin were suspended in a mixture of 20 ml water and 10 ml conc. HCl and stirred at 80° C. After 3 hrs the mixture was cooled to room temperature, diluted with 50 ml methanol and filtered. The filtrate was further diluted with 50 ml water and adjusted to pH ~12 by addition of ammonia. Resulting precipitate was again filtered off over a small pad of silica, and the filtrate was evaporated. The residue was dissolved in methanol/dichloromethane 2:1 and filtered once more over a pad of silica. The filtrate was finally evaporated and the residue used as such without further purification for the next step.

Yield 195 mg of 60% purity

[2-(4-Methylsulfanyl-phenyl)-3H-imidazo[4,5-b]pyridin-6-yl]-carbamic acid isopropyl ester 30 mg from example 4-1b) were dissolved in 0.5 ml dry N-methylpyrrolidone (NMP) and cooled in an ice bath. 0.08 ml of a 1M solution of isopropyl chloro formate in toluene were added. After stirring for 30 min, the temperature was raised to room temperature. After another 2 hrs, 0.2 ml conc. ammonia were added and the mixture was stirred 30 min. The solvents were removed under vacuum and the residue was purified by preparative HPLC-MS.

Yield 2 mg.

¹H-NMR (400 MHz, $D_6$-DMSO): δ=13.40 (broad s) and 12.92 (broad s, together 1H); 9.75 (broad s, 1H); 8.34 (s, 1H); 8.16-8.10 (m, 3H); 7.43 (d, 2H); 4.94 (m, 1H); 2.57 (s, 3H); 1.28 (d, 6H).

Example 5-1

[2-(3-Amino-phenyl)-3H-imidazo[4,5-b]pyridin-6-yl]-carbamic acid isopropyl ester 89 mg of the nitro-phenyl derivative from example 2-4 in 5 ml tetrahydrofuran (THF) and 5 ml methanol were hydrogenated over 33 mg 10% Pd on charcoal at room temperature for 45 min. The catalyst was filtered off and washed with methanol. The filtrate was evaporated and the residue purified by chromatography on silica in methanol/dichloromethane mixtures.

Yield 45 mg

¹H-NMR (400 MHz, $D_6$-DMSO): δ=13.24 (broad s) and 12.78 (broad s, together 1H); 9.79 (broad s) and 9.65 (broad s, together 1H); 8.33 (broad s, 1H); 8.14 (s, 1H); 7.45 (m, 1H); 7.30 (m, 1H); 7.20 (m, 1H); 6.70 (d, 1H); 5.33 (broad s, 2H); 4.93 (m, 1H); 1.28 (d, 6H).

The following examples were obtained in analogous fashion as described for example 5-1:

| Example-No. | Systematic Name | ¹H-NMR |
|---|---|---|
| 5-2 | [2-(4-Amino-phenyl)-3H-imidazo[4,5-b]pyridin-6-yl]-carbamic acid isopropyl ester | (400 MHz, $CD_3OD$): δ = 8.23 (broad s, 2H); 7.87 (broad s, 2H); 6.80 (broad s, 2H); 5.00 (m, not separated from H2O); 1.34 (d, 6H). |

Example 6-1

[2-(3-Acetylamino-phenyl)-3H-imidazo[4,5-b]pyridin-6-yl]-carbamic acid isopropyl ester 10 mg of the product from example 5-1 were dissolved in 1 ml dry pyridine and 7 μl acetyl chloride were added at room temperature. After stirring over night, the solvent was evaporated and the residue dissolved in 3 ml methanol. 1 ml conc. ammonia were added and the mixture stirred for 1 hr at room temperature.

¹H-NMR (400 MHz, $D_6$-DMSO): δ=13.10 (broad s, 1H); 10.25 (s, 1H); 9.92 (broad s) and 9.80 (broad s, together 1H);

8.57 (s, 1H); 8.45 (s, 1H); 8.27 (s, 1H); 7.89 (broad s, 1H); 7.79 (m, 1H); 7.57 (t, 1H); 5.02 (m, 1H); 2.19 (s, 3H); 1.38 (d, 6H).

Example 7-1

[2-(3-Methanesulfonylamino-phenyl)-3H-imidazo[4,5-b]pyridin-6-yl]-carbamic acid isopropyl ester 45 mg of the product from example 5-1 were dissolved in 1 ml dry NMP and cooled to 0° C. 18.3 mg methylsulfonylchloride were added and the mixture was stirred for 1 hr at 0° C. and another hr at room temperature. 12 µl (1 equivalent) pyridine were added and stirring was continued for another 60 min. After addition of 0.1 ml conc. HCl, the solvent was removed under vacuum and the residue purified by chromatography on C-18 RP silica in methanol water mixtures.
Yield 23 mg.
Melting point: m.p.=244° C.

Example 8-1

[2-(3-Methylsulfinyl-phenyl)-3H-imidazo[4,5-b]pyridin-6-yl]-carbamic acid isopropyl ester 97 mg meta-chloro perbenzoic acid (70%) were dissolved in 10 ml dichloromethane and dried by filtration over sodium sulfate. This solution was added to a suspension of 150 mg of the product from example 3-3 in 20 ml dichloromethane at room temperature. After 3 hrs the solvent was removed and the residue purified by chromatography on silica.
$^1$H-NMR (400 MHz, D$_6$-DMSO): δ=13.20 (broad s, 1H); 9.80 (broad s, 1H); 8.50 (s, 1H); 8.39 (s, 1H); 8.31 (d, 1H); 8.21 (s, 1H); 7.83-7.75 (m, 2H); 4.95 (m, 1H); 2.84 (s, 3H); 1.29 (d, 6H).

Example 8-2

[2-(3-Methylsulfonyl-phenyl)-3H-imidazo[4,5-b]pyridin-6-yl]-carbamic acid isopropyl ester 210 mg Oxone were added to a suspension of 130 mg of the product from example 3-3 in 20 ml methanol and 0.5 ml water. The mixture was stirred at room temperature for 30 min, then evaporated and the residue chromatographed on silica, eluting first with ethyl acetate, followed by ethyl acetate/methanol mixtures.
$^1$H-NMR (400 MHz, D6-DMSO): δ=13.72 (broad s) and 13.30 (broad s, together 1H); 9.87 (broad s) and 9.73 (broad s, together 1H); 8.76 (s) and 8.69 (s, together 1H); 8.51 (m, 1H); 8.48 (s, 1H); 8.23 (s, 1H); 8.07 (m, 1H); 7.86 (m, 1H); 4.95 (m, 1H); 2.51 (s, not separated from DMSO); 1.29 (d, 6H).

The following examples were obtained in analogous fashion as described for example 8-2:

| Example-No. | Systematic Name | $^1$H-NMR | Melting point (° C.) |
|---|---|---|---|
| 8-3 | [2-(4-Methanesulfonyl-phenyl)-3H-imidazo[4,5-b]pyridin-6-yl]-carbamic acid isopropyl ester | (400 MHz, D$_6$-DMSO): δ = 9.85 (broad s, 1H); 8.42 (broad s, 3H); 8.24 (s, 1H); 8.12 (d, 2H); 4.95 (m, 1H); 2.53 (s, not separated from DMSO); 1.29 (d, 6H). | |
| 8-4 | [2-(4-Methanesulfinyl-phenyl)-3H-imidazo[4,5-b]pyridin-6-yl]-carbamic acid isopropyl ester | (400 MHz, D$_6$-DMSO): δ = 13.20 (broad s, 1H); 9.80 (broad s, 1H); 8.37 (m, 3H); 8.21 (s, 1H); 7.87 (d, 2H); 4.95 (m, 1H); 2.82 (s, 3H); 1.29 (d, 6H). | |

Example 9-1

(2-Phenyl-1H-pyrrolo[2,3-b]pyridin-5-yl)-carbamic acid isopropyl ester a) 5-Nitro-3-phenylethynyl-pyridin-2-ylamine 1.83 g 2-amino-3-bromo-5-nitropyridine 0.29 g PdCl$_2$(PPh$_3$)$_2$ and 79 mg CuI were mixed in 36 ml dry THF and 3.45 ml triethylamine and 1.12 g phenylacetylene were added. Stirring was continued at room temperature for 12 hrs, then the solvent was removed and the residue purified by flash chromatography on silica in ethyl acetate/heptane eluent.
Yield 855 mg.

b) 5-Nitro-2-phenyl-1H-pyrrolo[2,3-b]pyridine 0.843 g potassium tert. butylate in 15 ml dry NMP were treated with a solution of 0.855 g of the product from example 9-1a) in 15 ml NMP. The mixture was stirred at room temperature for 12 hrs, and then transferred onto a short column of ca. 150 g silica. The product was eluted sequentially with heptane, then heptane/ethyl acetate 1:1. Product containing fractions were collected and evaporated, and the residue dispersed in water. Filtration and washing of the filter residue with water and heptane yielded 0.55 g of the title product.

c) 2-Phenyl-1H-pyrrolo[2,3-b]pyridin-5-ylamine 200 mg of the product from example 9-1b) in 15 ml methanol were hydrogenated over 40 mg 10% Pd on charcoal at room temperature for 2.5 hrs. The mixture was filtered and the product purified by chromatography on C-18 RP silica in methanol water.
Yield 107 mg (2-Phenyl-1H-pyrrolo[2,3-b]pyridin-5-yl)-carbamic acid isopropyl ester 130 mg of the product from example 9-1c) were dissolved in 2.18 ml dry NMP and cooled to 0° C. One equivalent (0.607 ml) of a 1M solution of iso-propyl chloroformate in toluene were added dropwise and stirring was continued for 10 min at 0° C., and another 3 hrs at room temperature. 0.5 ml methanol and 0.5 ml conc. ammonia were added and the mixture was stirred for 1 hr at room temperature. Finally the solvents were removed under vacuum and the residue purified by preparative HPLC-MS.
Yield 100 mg.
$^1$H-NMR (400 MHz, D$_6$-DMSO): δ=12.05 (s, 1H); 9.51 (broad s, 1H); 8.23 (s, 1H); 8.07 (s, 1H); 7.92 (d, 2H); 7.46 (t, 2H); 7.34 (t, 1H); 6.89 (s, 1H); 4.92 (m, 1H); 1.28 (d, 6H).

Example 9-2

{2-[3-(2-Methoxy-ethoxy)-phenyl]-1H-pyrrolo[2,3-b]pyridin-5-yl}-carbamic acid isopropyl ester a) 3-[3-(2-methoxy-ethoxy)-phenylethynyl]-5-nitro-pyridin-2-ylamine 3-(2-Methoxy-ethoxy)-phenylacetylene (6.3 g, 36 mmol) was added to a solution of triethylamine (1.92 mL, 14 mmol), 2-amino-3-bromo-5-nitropyridine (4 g, 18 mmol), PdCl$_2$(PPh$_3$)$_2$ (966 mg, 1.38 mmol) and CuI (262 mg, 1.38 mmol) in anhydrous tetrahydrofuran (80 mL) in the dark. The mixture was stirred at room temperature for 48 hours then concentrated in vacuo and dissolved in dichloromethane (150 mL). The organic solution was washed with water (25 mL), dried over MgSO$_4$, filtered and concentrated in vacuo to 20% of its original volume and heptane (20 mL) was then added. The resultant yellow solid was filtered and dried to give 3-[3-(2-methoxy-ethoxy)-phenylethynyl]-5-nitro-pyridin-2-ylamine (4.2 g, 74% yield).

$^1$H-NMR (400 MHz, D$_6$-DMSO): δ=8.89 (1H, d, J 2.7), 8.34 (1H, d, J 2.7), 7.39 (1H, m), 7.35 (1H, d, J 8.0), 7.30 (1H, dt, J 1.0, 7.6), 7.04 (1H, ddd, J 1.0, 2.6, 8.2), 4.15 (2H, t, J 4.5), 3.69 (2H, t, J 4.5), 3.34 (3H, s).

MS: M=(ES+) 314 (M+H), 355 (M+acetonitrile)

b) 2-[3-(2-methoxy-ethoxy)-phenyl]-5-nitro-1H-pyrrolo[2,3-b]pyridine

Potassium tert-butoxide (1.18 g, 10.5 mmol) was added to a solution of 3-[3-(2-methoxy-ethoxy)-phenylethynyl]-5-nitro-pyridin-2-ylamine (1.57 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with ethyl acetate then 10% methanol in ethyl acetate. The organics were concentrated in vacuo to 5% of their original volume and water (30 mL) was added. The resultant orange solid was filtered and dried to afford 2-[3-(2-methoxy-ethoxy)-phenyl]-5-nitro-1H-pyrrolo[2,3-b]pyridine (1.3 g, 83%).

$^1$H-NMR (400 MHz, D$_6$-DMSO): δ=12.88 (1H, s), 9.04 (1H, d, J 2.6), 8.77 (1H, d, J 2.6), 7.52-7.50 (2H, m), 7.36 (1H, app. t, J 8.1, 7.8), 7.18 (1H, s), 6.95 (1H, dd, J 1.8, 8.1), 4.15 (2H, t, J 4.6), 3.65 (2H, t, J 4.6), 3.25 (3H, s).

MS: M=(ES+) 314 (M+H), 355 (M+acetonitrile)

c) 2-[3-(2-methoxy-ethoxy)-phenyl]-1H-pyrrolo[2,3-b]pyridin-5-ylamine

To a mixture of 2-[3-(2-methoxy-ethoxy)-phenyl]-5-nitro-1H-pyrrolo[2,3-b]pyridine (7.1 mmol, 2.2 g) and iron powder (6.7 g) in ethanol (50 mL) was added HCl (conc.) (0.7 mL) and water (5 mL). The mixture was heated at 70° C. for 3 hours then cooled and filtered through Celite®. The solvent was removed in vacuo and the residue dissolved in ethyl acetate (30 mL), washed with saturated sodium bicarbonate (15 mL), dried over MgSO$_4$, filtered and concentrated in vacuo. The crude product was purified by column chromatography (SiO$_2$, ethyl acetate) to afford 2-[3-(2-methoxy-ethoxy)-phenyl]-1H-pyrrolo[2,3-b]pyridin-5-ylamine (1.2 g, 60%).

$^1$H-NMR (400 MHz, D$_6$-DMSO): δ=11.62 (1H, s), 7.78 (1H, d, J 2.0), 7.53-7.50 (2H, m), 7.38 (1H, app. t, J 8.0), 7.13 (1H, d, J 2.3), 6.93 (1H, dd, J 1.7, 8.0), 6.75 (1H, d, J 2.0), 4.8 (2H, br.s), 4.24 (2H, t, J 4.6), 3.76 (2H, t, J 4.6), 3.40 (3H, s).

MS: M=(ES+) 284 (M+H)

{2-[3-(2-Methoxy-ethoxy)-phenyl]-1H-pyrrolo[2,3-b]pyridine-5-yl}-carbamic acid isopropyl ester The above amino compound was acylated with isopropyl chloroformate as described for example 9-1 to yield the title compound.

$^1$H-NMR (400 MHz, D$_6$-DMSO): δ=12.00 (s, 1H); 9.52 (broad s; 1H); 8.22 (broad s, 1H); 8.06 (broad s, 1H); 7.52 (s) and 7.49 (s, together 2H); 7.36 (t, 1H); 6.92 (broad s, 2H); 4.92 (m, 2H); 4.20 (t, 2H); 3.71 (t, 2H); 1.28 (d, 6H).

The following examples were obtained in analogous fashion as described for example 9-2:

| Example-No. | Systematic Name | $^1$H-NMR | Melting point (° C.) |
|---|---|---|---|
| 9-3 | (2-Phenyl-1H-pyrrolo[2,3-b]pyridin-5-yl)-carbamic acid 2,2-dimethyl-propyl ester | (400 MHz, D$_6$-DMSO): δ = 11.94 (s, 1H); 9.45 (broad s, 1H); 8.14 (broad s, 1H); 7.97 (broad s, 1H); 7.83 (d, 2H); 7.37 (t, 2H); 7.25 (t, 1H); 6.80 (s, 1H); 3.73 (s, 2H); 0.87 (s, 9H). | |
| 9-4 | {2-[4-(2-Methoxy-ethoxy)-phenyl]-1H-pyrrolo[2,3-b]pyridin-5-yl}-carbamic acid ethyl ester | (400 MHz, CD$_3$OD): δ = 8.15 (broad s, 1H); 8.06 (broad s, 1H); 7.79 (d, 2H); 7.06 (d, 2H); 6.69 (s, 1H); 4.23 (q) and 4.19 (t, together 4H); 3.79 (t, 2H); 3.46 (s, 3H); 1.35 (t, 3H). | |
| 9-5 | {2-[4-(2-Methoxy-ethoxy)-phenyl]-1H-pyrrolo[2,3-b]pyridin-5-yl}-carbamic acid allyl ester | (400 MHz, CD$_3$OD): δ = 8.08 (broad s, 1H); 7.99 (broad s, 1H); 7.71 (d, 2H); 6.98 (d, 2H); 6.62 (s, 1H); 5.96 (m, 1H); 5.32 (d, 1H); 5.18 (d, 1H); 4.60 (d, 2H); 4.12 (t, 2H); 3.71 (t, 2H); 3.38 (s, 3H). | |
| 9-6 | {2-[3-(2-Methoxy-ethoxy)-phenyl]-1H- | (400 MHz, D$_6$-DMSO): δ = 11.88 (s, 1H); 9.46 (broad s; | |

-continued

| Example-No. | Systematic Name | ¹H-NMR | Melting point (° C.) |
|---|---|---|---|
| | pyrrolo[2,3-b]pyridin-5-yl}-carbamic acid ethyl ester | 1H); 8.09 (broad s, 1H); 7.92 (broad s, 1H); 7.39 (s) and 7.36 (s, together 2H); 7.23 (t, 1H); 6.78 (m, 2H); 4.07-3.99 (m, 4H); 3.58 (t, 2H); 1.14 (t, 3H). | |
| 9-7 | {2-[3-(2-Methoxy-ethoxy)-phenyl]-1H-pyrrolo[2,3-b]pyridin-5-yl}-carbamic acid allyl ester | (400 MHz, $D_6$-DMSO): $\delta$ = 12.23 (s, 1H); 9.92 (broad s; 1H); 8.43 (broad s, 1H); 8.26 (broad s, 1H); 7.73 (s) and 7.70 (s, together 2H); 7.57 (t, 1H); 7.14-7.11 (m, 2H); 6.27-6.17 (m, 1H); 5.59 (d, 1H); 5.46 (d, 1H); 4.84 (d, 2H); 4.40 (t, 2H); 3.92 (t, 2H). | |
| 9-8 | (2-Phenyl-1H-pyrrolo[2,3-b]pyridin-5-yl)-carbamic acid benzyl ester | | |
| 9-9 | {2-[3-(2-Methoxy-ethoxy)-phenyl]-1H-pyrrolo[2,3-b]pyridin-5-yl}-carbamic acid isobutyl ester | (400 MHz, $D_6$-DMSO): $\delta$ = 11.89 (s, 1H); 9.48 (broad s; 1H); 8.11 (broad s, 1H); 7.94 (broad s, 1H); 7.41-7.38 (m, 2H); 7.24 (t, 1H); 6.81-6.78 (m, 2H); 4.07 (t, 2H); 3.78 (d, 2H); 3.59 (t, 2H); 1.83 (m, 1H); 0.84 (d, 6H). | |
| 9-10 | {2-[3-(2-Methoxy-ethoxy)-phenyl]-1H-pyrrolo[2,3-b]pyridin-5-yl}-carbamic acid 2-chloro-benzyl ester | (400 MHz, $D_6$-DMSO): $\delta$ = 12.04 (s, 1H); 9.85 (broad s; 1H); 8.24 (broad s, 1H); 8.08 (broad s, 1H); 7.63-7.48 (m, 4H); 7.47-7.33 (m, 3H); 6.94-6.90 (m, 2H); 5.27 (s, 2H); 4.20 (t, 2H); 3.71 (d, 2H). | |
| 9-11 | (2-Phenyl-1H-pyrrolo[2,3-b]pyridin-5-yl)-carbamic acid ethyl ester | (400 MHz, $D_6$-DMSO): $\delta$ = 12.05 (s, 1H); 9.58 (broad s; 1H); 8.23 (broad s, 1H); 8.06 (broad s, 1H); 7.93 (d, 2H); 7.47 (t, 2H); 7.35 (t, 1H); 6.90 (s, 1H); 4.16 (6, 2H); 1.27 (t, 3H). | |
| 9-12 | (2-Phenyl-1H-pyrrolo[2,3-b]pyridin-5-yl)-carbamic acid 2-chloro-benzyl ester | (400 MHz, $D_6$-DMSO): $\delta$ = 12.07 (s, 1H); 9.85 (broad s; 1H); 8.24 (broad s, 1H); 8.09 (broad s, 1H); 7.93 (d, 2H); 7.64-7.32 (m, 7H); 6.91 (s, 1H). | |
| 9-13 | (2-Phenyl-1H-pyrrolo[2,3-b]pyridin-5-yl)-carbamic acid allyl ester | (400 MHz, $D_6$-DMSO): $\delta$ = 12.28 (s, 1H); 9.93 (broad s; 1H); 8.44 (broad s, 1H); 8.28 (broad s, 1H); 8.14 (d, 2H); 7.69 (t, 2H); 7.57 (t, 1H); 7.12 (s, 1H); 6.23 (m, 1H); 5.60 (d, 1H); 5.47 (d, 1H); 4.85 (d, 2H). | |
| 9-14 | (2-Phenyl-1H-pyrrolo[2,3-b]pyridin-5-yl)-carbamic acid isobutyl ester | (400 MHz, $D_6$-DMSO): $\delta$ = 12.05 (s, 1H); 9.56 (broad s; 1H); 8.23 (broad s, 1H); 8.06 (broad s, 1H); 7.93 (d, 2H); 7.47 (t, 2H); 7.35 (t, 1H); 6.90 (s, 1H); 3.90 (d, 2H); 1.95 (m, 1H); 0.96 (d, 6H). | |
| 9-15 | {2-[3-(2-Methoxy-ethoxy)-phenyl]-1H-pyrrolo[2,3-b]pyridin-5-yl}-carbamic acid 2,2-dimethyl-propyl ester | (400 MHz, $D_6$-DMSO): $\delta$ = 12.21 (s, 1H); 9.77 (broad s; 1H); 8.45 (broad s, 1H); 8.27 (broad s, 1H); 7.74-7.70 (m, 2H); 7.57 (t, 1H); 7.14-7.11 (m, 2H); 4.40 (t, 2H); 4.03 (s, 2H); 3.91 (t, 2H); 1.18 (d, 9H). | |

| Example-No. | Systematic Name | ¹H-NMR | Melting point (° C.) |
|---|---|---|---|
| 9-16 | {2-[3-(2-Methoxy-ethoxy)-phenyl]-1H-pyrrolo[2,3-b]pyridin-5-yl}-carbamic acid benzyl ester | (400 MHz, D$_6$-DMSO): δ = 12.03 (s, 1H); 9.76 (broad s; 1H); 8.23 (broad s, 1H); 8.07 (broad s, 1H); 7.53-7.33 (m, 8H); 6.94-6.91 (m, 2H); 5.19 (s, 2H); 4.20 (t, 2H); 3.71 (t, 2H). | |
| 9-17 | {2-[4-(2-Methoxy-ethoxy)-phenyl]-1H-pyrrolo[2,3-b]pyridin-5-yl}-carbamic acid isopropyl ester | (400 MHz, CD$_3$OD): δ = 8.11 (broad s, 1H); 8.05 (broad s, 1H); 7.79 (d, 2H); 7.06 (d, 2H); 6.69 (s, 1H); 4.99 (m, not separated from H2O) 4.20 (t, 2H); 3.80 (t, 2H); 3.46 (s, 3H); 1.34 (d, 6H). | |
| 9-18 | {2-[4-(2-Methoxy-ethoxy)-phenyl]-1H-pyrrolo[2,3-b]pyridin-5-yl}-carbamic acid benzyl ester | (400 MHz, CD$_3$OD): δ = 8.16 (broad s, 1H); 8.08 (broad s, 1H); 7.79 (d, 2H); 7.46 (d, 2H); 7.42-7.32 (m, 3H); 7.06 (d, 2H); 6.69 (s, 1H); 5.23 (s, 2H); 4.20 (t, 2H); 3.80 (t, 2H); 3.46 (s, 3H); 1.34 (d, 6H). | |
| 9-19 | {2-[4-(2-Methoxy-ethoxy)-phenyl]-1H-pyrrolo[2,3-b]pyridin-5-yl}-carbamic acid isobutyl ester | (400 MHz, CD$_3$OD): δ = 8.16 (broad s, 1H); 8.06 (broad s, 1H); 7.79 (d, 2H); 7.06 (d, 2H); 6.69 (s, 1H); 4.20 (t, 2H); 3.97 (d, 2H); 3.80 (t, 2H); 3.46 (s, 3H); 2.02 (m, 1H); 1.03 (d, 6H). | |

Example 9-20

[2-(3-Acetylamino-phenyl)-1H-pyrrolo[2,3-b]pyridin-5-yl]-carbamic acid isopropyl ester Was prepared analogously to example 9-2 starting from 3-(acetylamino)phenylacetylene. In the preparation of the intermediate N-[3-(5-nitro-1H-pyrrolo[2,3-b]pyridin-2-yl)-phenyl]-acetamide by cyclization reaction an higher equimolar amount of base (Potassium tert-butoxide) as in Example 2-2 is needed:

Preparation of N-[3-(5-nitro-1H-pyrrolo[2,3-b]pyridin-2-yl)-phenyl]-acetamide

Potassium tert-butoxide (2.25 g, 20 mmol) was added to a solution of N-[4-(2-amino-5-nitro-pyridin-3-ylethynyl)-phenyl]-acetamide (1.48 g, 5 mmol) in a 2:1 mixture of tetrahydrofuran and dimethylformamide (75 mL). The mixture was heated at 70° C. for 16 hours then the tetrahydrofuran was removed in vacuo. The mixture was poured onto a pad of silica and eluted with 10% methanol in ethyl acetate. The organics were concentrated in vacuo to 5% of their original volume and water (30 mL) was added. The resultant orange solid was filtered and dried to afford N-[3-(5-Nitro-1H-pyrrolo[2,3-b]pyridin-2-yl)-phenyl]-acetamide (1.01 g, 68%).

¹H-NMR (400 MHz, D$_6$-DMSO): δ=12.97 (1H, s), 10.17 (1H, s), 9.16 (1H, d, J 2.5), 8.94 (1H, d, J 2.5), 8.24 (1H, s), 7.70 (1H, d, J 7.8), 7.63 (1H, d, J 8.2), 7.50 (1H, app. t, J 7.9), 7.10 (1H, s), 2.15 (3H, s).

MS: M=(ES+) 297 (M+H), 338 (M+acetonitrile), 593 (2M+H), 889 (3M+H)

[2-(3-Acetylamino-phenyl)-1H-pyrrolo[2,3-b]pyridin-5-yl]-carbamic acid isopropyl ester The above nitro compound was reduced to the amino compound and subsequently acylated with isopropyl chloroformate as described in example 9-1 to yield the title compound.

¹H-NMR (400 MHz, D$_6$-DMSO): δ=12.03 (s, 1H); 10.05 (broad s; 1H); 9.53 (broad s, 1H); 8.22 (broad s, 1H); 8.06 (broad s, 2H); 7.56 (t, 2H); 7.39 (t, 1H); 6.73 (s, 1H); 4.92 (heptett, 1H); 2.09 (s, 3H); 1.28 (d, 6H).

The following examples were obtained in analogous fashion as described for example 9-20:

| Example-No. | Systematic Name | ¹H-NMR | Melting point (° C.) |
|---|---|---|---|
| 9-21 | [2-(4-Acetylamino-phenyl)-1H-pyrrolo[2,3-b]pyridin-5-yl]-carbamic acid allyl ester | (400 MHz, D$_6$-DMSO): δ = 11.81 (s, 1H); 9.94 (s; 1H); 9.54 (broad s, 1H); 8.05 (broad s, 1H); 7.88 (broad s, 1H); 7.70 (d, 2H); 7.52 (d, 2H); 6.65 (s, 1H); 5.87 (m, | |

-continued

| Example-No. | Systematic Name | ¹H-NMR | Melting point (° C.) |
|---|---|---|---|
| | | 1H); 5.24 (d, 1H); 5.11 (d, 1H); 4.49 (d, 2H); 1.93 (s, 3H). | |
| 9-22 | [2-(3-Acetylamino-phenyl)-1H-pyrrolo[2,3-b]pyridin-5-yl]-carbamic acid 2-chloro-benzyl ester | (400 MHz, D₆-DMSO): δ = 12.06 (s, 1H); 10.06 (broad s; 1H); 9.84, (broad s, 1H); 8.23 (broad s, 1H); 8.10 (s) and 8.07 (s, together 2H); 7.64-7.50 (m, 4H); 7.46-7.35 (m, 3H); 6.74 (s, 1H); 5.27 (s, 2H); 2.09 (s, 3H). | |
| 9-23 | [2-(3-Acetylamino-phenyl)-1H-pyrrolo[2,3-b]pyridin-5-yl]-carbamic acid benzyl ester | (400 MHz, D₆-DMSO): δ = 12.05 (s, 1H); 10.06 (broad s; 1H); 9.75, (broad s, 1H); 8.23 (broad s, 1H); 8.09 (s) and 8.07 (s, together 2H); 7.56 (t, 2H); 7.49-7.34 (m, 6H); 6.74 (s, 1H); 5.19 (s, 2H); 2.09 (s, 3H). | |
| 9-24 | [2-(3-Acetylamino-phenyl)-1H-pyrrolo[2,3-b]pyridin-5-yl]-carbamic acid 2,2-dimethyl-propyl ester | (400 MHz, D₆-DMSO): δ = 11.89 (s, 1H); 9.91 (s, 1H); 9.43 (broad s; 1H); 8.09 (broad s, 1H); 7.93 (broad s, 2H); 7.44 (d, 1H); 7.39 (d, 1H); 7.25 (t, 1H); 6.59 (s, 1H); 3.68 (s, 2H); 1.95 (s, 3H); 0.83 (s, 9H). | |
| 9-25 | [2-(4-Acetylamino-phenyl)-1H-pyrrolo[2,3-b]pyridin-5-yl]-carbamic acid 2,2-dimethyl-propyl ester | (400 MHz, D₆-DMSO): δ = 11.92 (s, 1H); 10.07 (s, 1H); 9.53 (broad s; 1H); 8.19 (broad s, 1H); 8.02 (broad s, 1H); 7.83 (d, 2H); 7.65 (d, 2H); 6.78 (s, 1H); 3.81 (s, 2H); 2.06 (s, 3H); 0.96 (s, 9H). | |
| 9-26 | [2-(3-Acetylamino-phenyl)-1H-pyrrolo[2,3-b]pyridin-5-yl]-carbamic acid ethyl ester | (400 MHz, D₆-DMSO): δ = 11.87 (s, 1H); 9.89 (broad s; 1H); 9.42 (broad s, 1H); 8.05 (broad s, 1H); 7.90 (broad s, 2H); 7.41 (d, 1H); 7.37 (d, 1H); 7.22 (t, 1H); 6.57 (s, 1H); 3.98 (q, 2H); 1.92 (s, 3H); 1.11 (t, 3H). | |
| 9-27 | [2-(3-Acetylamino-phenyl)-1H-pyrrolo[2,3-b]pyridin-5-yl]-carbamic acid allyl ester | (400 MHz, D₆-DMSO): δ = 12.05 (s, 1H); 10.05 (broad s; 1H); 9.70 (broad s, 1H); 8.22 (broad s, 1H); 8.07 (broad s, 2H); 7.56 (t, 2H); 7.39 (t, 1H); 6.74 (s, 1H); 6.03 (m, 1H); 5.39 (d, 1H); 5.26 (d, 1H); 4.64 (d, 2H); 2.09 (s, 3H). | |
| 9-28 | [2-(3-Acetylamino-phenyl)-1H-pyrrolo[2,3-b]pyridin-5-yl]-carbamic acid isobutyl ester | (400 MHz, D₆-DMSO): δ = 12.03 (s, 1H); 10.05 (broad s; 1H); 9.59 (broad s, 1H); 8.22 (broad s, 1H); 8.07 (broad s, 2H); 7.57 (t, 2H); 7.39 (t, 1H); 6.73 (s, 1H); 3.90 (d, 2H); 2.09 (s, 3H); 1.98 m, 1H); 0.96 (d, 6H). | |

Example 10-1

[2-(3,4-Difluoro-phenyl)-3H-imidazo[4,5-b]pyridin-6-yl]-carbamic acid isopropyl ester a) 2-(3,4-Difluoro-phenyl)-6-nitro-3H-imidazo[4,5-b]pyridine 1.00 g 2,3-diamino-5-nitro-pyridine and 0.95 g 3,4-difluorobenzaldehyde were stirred in 60 ml nitrobenzene at 160° C. for 26 hrs. The solvent was removed under vacuum and the residue dissolved in 40 ml pyridine at 60° C. The solution was cooled in an ice bath. Precipitated product was isolated by filtration and dried to yield 0.5 g of the title product.

b) 6-amino-2-(3,4-Difluoro-phenyl)-3H-imidazo[4,5-b]pyridine 60 mg of the above nitro compound were hydrogenated for 2 hrs at room temperature in a mixture of 15 ml methanol and 15 ml THF over palladium on charcoal. The catalyst was filtered off and the filtrate evaporated to give 56 mg of the title compound, which was used directly in the next reaction step.

[2-(3,4-Difluoro-phenyl)-3H-imidazo[4,5-b]pyridin-6-yl]-carbamic acid isopropyl ester 50 mg (0.16 mmol) of the above amino compound in 1 ml dry NMP were treated at room temperature dropwise with 0.16 ml (0.16 mmol) of a 1M solution of isopropyl chloroformate in toluene. After stirring for 3 hrs the solvents were removed under vacuum and the residue purified by preparative HPLC/MS, yielding 30 mg of the title product.

$^1$H-NMR (400 MHz, D$_6$-DMSO): δ=9.87 (broad s) and 9.74 (broad s, together 1H); 8.38 (s, 1H); 8.20 (m, 2H); 8.04 (broad d, 1H); 7.67 (q, 1H); 4.94 (m, 1H); 1.29 (d, 6H).

Example 10-2

(2-{4-[Bis-(2-methoxy-ethyl)-amino]-3-fluoro-phenyl}-3H-imidazo[4,5-b]pyridin-6-yl)-carbamic acid isopropyl ester a) [2-Fluoro-4-(6-nitro-3H-imidazo[4,5-b]pyridin-2-yl)-phenyl]-bis-(2-methoxy-ethyl)-amine 0.5 g 2-(3,4-Difluoro-phenyl)-6-nitro-3H-imidazo[4,5-b]pyridine, 0.1 ml NMP and 0.51 g bis(2-methoxyethyl)-amine were heated to 170° C. with stirring for 18 hrs. Volatile materials were removed under vacuum and the residue purified by chromatography, first on silica in dichloromethane/methanol mixtures, and subsequently by preparative HPLC.

Yield 42 mg of the title product (2-{4-[Bis-(2-methoxy-ethyl)-amino]-3-fluoro-phenyl}-3H-imidazo[4,5-b]pyridin-6-yl)-carbamic acid isopropyl ester The above nitro compound was hydrogenated to the amino compound and subsequently reacted with isopropyl chloroformate as described for 10-1 to give the title product.

$^1$H-NMR (400 MHz, CD$_3$OD): δ=8.27 (broad s, 2H); 7.79 (m, 2H); 7.14 (t, 1H); 5.02 (m, 1H); 3.61 (m, 8H); 3.35 (s, not separated from MeOH); 1.35 (d, 6H).

Example 11-1

3-(6-Isopropoxycarbonylamino-3H-imidazo[4,5-b]pyridin-2-yl)-benzoic acid was prepared starting from 3-carboxybenzaldehyde and 2,3-diamino-5-nitropyridine as described for 10-1. In the final step, after reacting with isopropyl chloroformate in NMP, the reaction mixture was treated with 100 mg sodium hydroxide and 1 ml water for 1 hr at room temperature. The crude product was precipitated by addition of 30 ml water and filtered off. It was further purified by dissolving in 50 ml aqueous sodium carbonate solution and washing with dichloromethane. The carbonate solution was acidified to pH 2-3 by addition acetic acid and HCl, and extracted with dichloromethane. The dichloromethane phase was evaporated to give 61 mg of the title product.

$^1$H-NMR (400 MHz, D$_6$-DMSO): δ=13.50 (broad s, 1H); 9.76 (broad s, 1H); 8.84 (s, 1H); 8.37 (s) and 8.33 (d, together 2H); 8.21 (s, 1H); 8.05 (d, 1H); 7.60 (t, 1H); 4.94 (m, 1H); 1.29 (d, 6H).

Example 11-2

{2-[3-(2-Methoxy-1-methoxymethyl-ethylcarbamoyl)-phenyl]-3H-imidazo[4,5-b]pyridin-6-yl}-carbamic acid isopropyl ester 25 mg (0.07 mmol) of the acid from example 11-1 in 1 ml dry DMF were treated with 18 mg (0.11 mmol) 1,1'-carbonyldiimidazole at room temperature for 2 hrs. 13 mg (0.11 mmol) 2-amino-1,3-dimethoxypropan were added and stirring was continued for 4 hrs. The solvent was removed under vacuum, the residue dissolved in dichloromethane and washed with aqueous sodium carbonate solution. The dichloromethane phase was evaporated and the residue purified by chromatography on silica in dichloromethane/methanol mixtures.

Yield 5 mg of the title product $^1$H-NMR (400 MHz, D$_6$-DMSO): δ=9.80 (broad s, 1H); 8.67 (s, 1H); 8.49 (broad s, 1H); 8.38 (s, 1H); 8.29 (d, 1H); 8.20 (s, 1H); 7.98 (d, 1H); 7.66 (t, 1H); 4.95 (m, 1H); 4.35 (m, 1H); 3.49 (m, 4H); 3.29 (s, not separated from H$_2$O); 1.29 (d, 6H).

Analogously was prepared:

Example 11-3

{2-[3-(3-Methoxy-propylcarbamoyl)-phenyl]-3H-imidazo[4,5-b]pyridin-6-yl}-carbamic acid isopropyl ester $^1$H-NMR (400 MHz, D$_6$-DMSO): δ=13.12 (broad s) and 12.00 (broad s, together 1H); 9.78 (broad s, 1H); 8.66 (broad s, 2H); 8.38 (s, 1H); 8.29 (d, 1H); 8.20 (s, 1H); 7.95 (d, 1H); 7.65 (t, 1H); 4.95 (m, 1H); 3.41-3.30 (t and m, not separated from H$_2$O); 3.26 (s, 3H); 1.80 (m, 2H); 1.29 (d, 6H).

Example 12-1

[2-(2-Chloro-pyridin-4-yl)-3H-imidazo[4,5-b]pyridin-6-yl]-carbamic acid isopropyl ester a) 2-(2-Chloro-pyridin-4-yl)-6-nitro-3H-imidazo[4,5-b]pyridine was prepared as described for example 4-1, starting from 2-chloropyridine-4-carboxylic acid and 2,3-diamino-5-nitropyridine.

b) 2-(2-Chloro-pyridin-4-yl)-6-amino-3H-imidazo[4,5-b]pyridine was prepared by reduction of the above nitro compound with iron powder as described for example 1-1.

[2-(2-Chloro-pyridin-4-yl)-3H-imidazo[4,5-b]pyridin-6-yl]-carbamic acid isopropyl ester was prepared from the above amino compound and isopropyl chloroformate as described for example 10-1.

$^1$H-NMR (400 MHz, D$_6$-DMSO): δ=13.90 (broad s) and 12.43 (broad s, together 1H); 9.95 (broad s) and 9.81 (broad s, together 1H); 8.61 (s, 2H); 8.46 (s, 1H); 8.27 (s, 1H); 8.18 (broad s (and 8.12 (broad s, together 1H); 4.95 (m, 1H); 1.29 (d, 6H).

Example 12-2

{2-[2-(3-Methoxy-propylamino)-pyridin-4-yl]-3H-imidazo[4,5-b]pyridin-6-yl}-carbamic acid isopropyl ester a) (3-Methoxy-propyl)-[4-(6-nitro-3H-imidazo[4,5-b]pyridin-2-yl)-pyridin-2-yl]-amine 1.20 g (4.35 mmol) 2-(2-Chloro-pyridin-4-yl)-6-nitro-3H-imidazo[4,5-b]pyridine in 12 ml dry NMP and 1.18 g (13 mmol) 3-methoxypropylamine were heated to 200° C. in a closed vessel in a microwave reactor for 30 min. The solvent was removed under vacuum and the residue dissolved in a mixture of 20 ml ethyl acetate and 30 ml 5% aqueous HCl. The HCl phase was separated and brought to alkaline pH by addition of conc. ammonia. The alkaline aqueous phase was extracted with dichloromethane, and the organic phases were combined and dried. Evaporation and chromatography of the residue on silica in ethyl acetate/methanol mixtures gave 480 mg of the title product.

b) 2-[2-(3-Methoxy-propylamino)-pyridin-4-yl]-3H-imidazo[4,5-b]pyridin-6-ylamine The above nitro compound was reduced with iron powder as described in example 1-1 and purified by chromatography on silica in ethyl acetate/methanol mixtures.

Yield 360 mg of the title product {2-[2-(3-Methoxy-propylamino)-pyridin-4-yl]-3H-imidazo[4,5-b]pyridin-6-yl}-carbamic acid isopropyl ester 170 mg (0.57 mmol) of the above amino compound were dissolved in 3 ml NMP and treated at 0° C. with 0.855 ml of a 1M solution (0.85 mmol) of isopropyl chloroformate in toluene. Stirring was continued at room temperature for 2 hrs, then methanol and a few ml of conc. ammonia were added and the mixture was stirred for another hr. Evaporation and chromatography on silica in ethyl acetate/methanol mixtures gave 88 mg of the title product.

$^1$H-NMR (400 MHz, D$_6$-DMSO): δ=13.59 (s) and 13.08 (s, together 1H); 9.87 (broad s) and 9.73 (broad s, together 1H); 8.39 (d, 2H); 8.21 (s, 1H); 8.13 (t, 1H); 7.21 (d) and 7.17 (dd, together 1H); 6.79 (dt, 1H, exchanges with D2O); 4.94 (m, 1H); 3.43 (t, 2H); 3.34 (m, not separated from H2O); 3.25 (s, 3H); 1.81 (m, 2H); 1.29 (d, 6H).

LIST OF REFERENCES

Avizienyte, E., et al., Nature Cell Bio. 4 (2002) 632-638
Bastin, R. J., et al., Organic Proc. Res. Dev. 4 (2000) 427-435
Biscardi, J. S., et al., Adv. Cancer Res. 76 (2000) 61-119
Boyce, B. F., et al., J. Clin., Invest. 90 (1992) 1622-1627
Cai, S. X., et al, J. Med. Chem. 40 (1997) 3679-3686
Eliceiri, B. P., et al., Mol. Cell. 4 (1999) 915-924
Ellis, L. M., et al., J. Biol. Chem. 273 (1998) 1052-1057
Magdolen, P., et al., Tetrahedron 57 (2001) 4781-4785
Missbach, M., et al., Bone-24 (1999) 437-449
Nam, J. S., et al., Clin. Cancer Res. 8 (2002) 2430-2-2436
Paul, R., et al., Nat. Med. 7 (2001) 222-227
Sawyer, T., et al., Expert Opin. Investig. Drugs 10 (2001) 1327-1344
Schwartzberg, P. L., Oncogene 17 (1998) 1463-1468
Soriano, P., et al., Cell 64 (1991) 693-702
Stahl, P. H., and Wermuth, G., (editors), Handbook of Pharmaceutical Salts, Verlag Helvetica Chimica Acta (VHCA), Zürich (2002)
Staley, C. A., Cell Growth Differ. 8 (1997) 269-274
Susva, M., et al., Trends Pharmacol. Sci. 21 (2000) 489-495
Tsuji, M., J. Org. Chem. 68 (2003) 9589-9597
US 2004/0242883
U.S. Pat. No. 4,162,265A
Weis, S., et al., J. Clin. Invest. 113 (2004) 885-894
WO 01/00213
WO 01/94341
WO 02/016352
WO 02/083668
WO 02/092573
WO 03/004492
WO 03/035065
WO 04/024897
WO 04/041823
WO 04/085436

---

The invention claimed is:
1. A compound according to formula I,

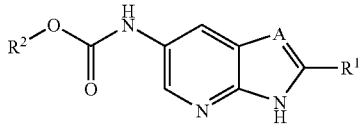

formula I wherein,
R¹ is a phenyl group optionally substituted with halogen, cyano, nitro, amino, —C(O)OH, heterocyclyl, —O-heterocyclyl, —S(O)₂NH₂, —X-alkyl or —Y-cycloalkyl; or a heteroaryl group optionally substituted with halogen, nitro, amino, heterocyclyl or —Z-alkyl;
and all alkyl groups are optionally substituted one or several times by halogen, hydroxy, alkoxy, amino, alkylamino, dialkylamino or alkylsulfonyl;
X is a single bond, —NR—, —O—, —S—, —CH₂—S(O)₂ NH—, —NHS(O)₂—, —S(O)₂NH—, —S(O)₂—, —S(O)—, —NRC(O)— or —C(O)NR—;
Y is —NRC(O)— or —C(O)NR—;
Z is a single bond, —NR— or —O—;
R is hydrogen or alkyl, wherein the alkyl is optionally substituted one or several times by halogen or alkoxy;
R² is alkyl, halogenated alkyl, alkenyl, alkynyl, cycloalkyl or phenylalkyl, wherein the phenyl group is optionally substituted one or several times by halogen, alkyl, alkoxy, halogenated alkyl, halogenated alkoxy or cyano;
A is =CH— or =N—;
or a pharmaceutically acceptable salt thereof.

2. A compound according to claim 1, wherein:
R¹ is a phenyl group optionally substituted one to three, preferably one or two times with halogen, nitro, amino, —C(O)OH, heterocyclyl, —S(O)₂NH₂, —X-alkyl; or a heteroaryl group optionally substituted one or two times with halogen, heterocyclyl or —Z-alkyl;
and all alkyl groups are optionally substituted one or two times by hydroxy, alkoxy or dialkylamino;
X is —NR—, —O—, —S—, —NHS(O)₂—, —S(O)₂—, —S(O)—, —NRC(O)— or —C(O)NR—;
Z is a single bond or —NR—;
R is hydrogen or alkyl, wherein the alkyl is optionally substituted one or two times by alkoxy; and
R² is alkyl, halogenated alkyl, alkenyl, alkynyl, cycloalkyl or phenylalkyl, wherein the phenyl group is optionally substituted one or two times by halogen.

3. A compound according to claim 1 wherein
R¹ is a phenyl group optionally substituted one to three, preferably one or two times with —X-alkyl; wherein the alkyl group is optionally substituted one or two times by alkoxy;
X is —O— or —NRC(O)—;
R is hydrogen;
R² is alkyl, alkenyl or phenylalkyl, wherein the phenyl group is optionally substituted one or two times by chlorine; and
A is =CH—.

4. A compound according to claim 3 selected from the group consisting of:
(2-Phenyl-1H-pyrrolo[2,3-b]pyridin-5-yl)-carbamic acid isopropyl ester;
{2-[3-(2-Methoxy-ethoxy)-phenyl]-1H-pyrrolo[2,3-b]pyridin-5-yl}-carbamic acid isopropyl ester;
(2-Phenyl-1H-pyrrolo[2,3-b]pyridin-5-yl)-carbamic acid 2,2-dimethyl-propyl ester;
{2-[4-(2-Methoxy-ethoxy)-phenyl]-1H-pyrrolo[2,3-b]pyridin-5-yl}-carbamic acid ethyl ester;
{2-[4-(2-Methoxy-ethoxy)-phenyl]-1H-pyrrolo[2,3-b]pyridin-5-yl}-carbamic acid allyl ester;
{2-[3-(2-Methoxy-ethoxy)-phenyl]-1H-pyrrolo[2,3-b]pyridin-5-yl}-carbamic acid ethyl ester;
{2-[3-(2-Methoxy-ethoxy)-phenyl]-1H-pyrrolo[2,3-b]pyridin-5-yl}-carbamic acid allyl ester;
(2-Phenyl-1H-pyrrolo[2,3-b]pyridin-5-yl)-carbamic acid benzyl ester;
{2-[3-(2-Methoxy-ethoxy)-phenyl]-1H-pyrrolo[2,3-b]pyridin-5-yl}-carbamic acid isobutyl ester;
{2-[3-(2-Methoxy-ethoxy)-phenyl]-1H-pyrrolo[2,3-b]pyridin-5-yl}-carbamic acid 2-chloro-benzyl ester;
(2-Phenyl-1H-pyrrolo[2,3-b]pyridin-5-yl)-carbamic acid ethyl ester;
(2-Phenyl-1H-pyrrolo[2,3-b]pyridin-5-yl)-carbamic acid 2-chloro-benzyl ester;
(2-Phenyl-1H-pyrrolo[2,3-b]pyridin-5-yl)-carbamic acid allyl ester;
(2-Phenyl-1H-pyrrolo[2,3-b]pyridin-5-yl)-carbamic acid isobutyl ester;
{2-[3-(2-Methoxy-ethoxy)-phenyl]-1H-pyrrolo[2,3-b]pyridin-5-yl}-carbamic acid 2,2-dimethyl-propyl ester;
{2-[3-(2-Methoxy-ethoxy)-phenyl]-1H-pyrrolo[2,3-b]pyridin-5-yl}-carbamic acid benzyl ester;
{2-[4-(2-Methoxy-ethoxy)-phenyl]-1H-pyrrolo[2,3-b]pyridin-5-yl}-carbamic acid isopropyl ester;
{2-[4-(2-Methoxy-ethoxy)-phenyl]-1H-pyrrolo[2,3-b]pyridin-5-yl}-carbamic acid benzyl ester;
{2-[4-(2-Methoxy-ethoxy)-phenyl]-1H-pyrrolo[2,3-b]pyridin-5-yl}-carbamic acid isobutyl ester;
[2-(3-Acetylamino-phenyl)-1H-pyrrolo[2,3-b]pyridin-5-yl]-carbamic acid isopropyl ester;
[2-(4-Acetylamino-phenyl)-1H-pyrrolo[2,3-b]pyridin-5-yl]-carbamic acid allyl ester;
[2-(3-Acetylamino-phenyl)-1H-pyrrolo[2,3-b]pyridin-5-yl]-carbamic acid 2-chloro-benzyl ester;
[2-(3-Acetylamino-phenyl)-1H-pyrrolo[2,3-b]pyridin-5-yl]-carbamic acid benzyl ester;
[2-(3-Acetylamino-phenyl)-1H-pyrrolo[2,3-b]pyridin-5-yl]-carbamic acid 2,2-dimethyl-propyl ester;
[2-(4-Acetylamino-phenyl)-1H-pyrrolo[2,3-b]pyridin-5-yl]-carbamic acid 2,2-dimethyl-propyl ester;
[2-(3-Acetylamino-phenyl)-1H-pyrrolo[2,3-b]pyridin-5-yl]-carbamic acid ethyl ester;
[2-(3-Acetylamino-phenyl)-1H-pyrrolo[2,3-b]pyridin-5-yl]-carbamic acid allyl ester; and
[2-(3-Acetylamino-phenyl)-1H-pyrrolo[2,3-b]pyridin-5-yl]-carbamic acid isobutyl ester.

5. A compound according to claim 1, wherein:
R¹ is a phenyl group optionally substituted one to three, preferably one or two, times with fluorine, nitro, amino, —C(O)OH, heterocyclyl, —S(O)₂NH₂, or —X-alkyl; wherein the alkyl group is optionally substituted one or two times by hydroxy, alkoxy or dialkylamino;
X is —NR—, —O—, —S—, —NHS(O)₂—, —S(O)₂—, —S(O)—, —NRC(O)— or —C(O)NR—;
R is hydrogen or alkyl, wherein the alkyl is optionally substituted one or two times by alkoxy;
R² is alkyl, halogenated alkyl, alkenyl, alkynyl, cycloalkyl or phenylalkyl, wherein the phenyl group is optionally substituted one or two times by halogen; and
A is =N—.

6. A compound according to claim 5 selected from the group consisting of:

(2-Phenyl-3H-imidazo[4,5-b]pyridin-6-yl)-carbamic acid 1-methyl-allyl ester;
(2-Phenyl-1H-imidazo[4,5-b]pyridin-6-yl)-carbamic acid isopropyl ester;
(2-Phenyl-3H-imidazo[4,5-b]pyridin-6-yl)-carbamic acid cyclohexyl ester;
(2-Phenyl-3H-imidazo[4,5-b]pyridin-6-yl)-carbamic acid isobutyl ester;
(2-Phenyl-3H-imidazo[4,5-b]pyridin-6-yl)-carbamic acid allyl ester;
(2-Phenyl-3H-imidazo[4,5-b]pyridin-6-yl)-carbamic acid tert-butyl ester;
(2-Phenyl-3H-imidazo[4,5-b]pyridin-6-yl)-carbamic acid cyclopentyl ester;
(2-Phenyl-3H-imidazo[4,5-b]pyridin-6-yl)-carbamic acid ethyl ester;
(2-Phenyl-3H-imidazo[4,5-b]pyridin-6-yl)-carbamic acid sec-butyl ester;
(2-Phenyl-3H-imidazo[4,5-b]pyridin-6-yl)-carbamic acid 1-ethyl-propyl ester;
(2-Phenyl-3H-imidazo[4,5-b]pyridin-6-yl)-carbamic acid 2,2,2-trifluoro-1-methyl-ethyl ester;
(2-Phenyl-3H-imidazo[4,5-b]pyridin-6-yl)-carbamic acid 2,2-dimethyl-propyl ester;
(2-Phenyl-3H-imidazo[4,5-b]pyridin-6-yl)-carbamic acid 1-phenyl-ethyl ester;
(2-Phenyl-1H-imidazo[4,5-b]pyridin-6-yl)-carbamic acid propyl ester;
(2-Phenyl-3H-imidazo[4,5-b]pyridin-6-yl)-carbamic acid 1-methyl-prop-2-ynyl ester;
(2-Phenyl-3H-imidazo[4,5-b]pyridin-6-yl)-carbamic acid 1-methyl-but-2-ynyl ester;
(2-Phenyl-3H-imidazo[4,5-b]pyridin-6-yl)-carbamic acid cyclobutyl ester;
(2-Phenyl-3H-imidazo[4,5-b]pyridin-6-yl)-carbamic acid 1,3-dimethyl-butyl ester;
(2-Phenyl-3H-imidazo[4,5-b]pyridin-6-yl)-carbamic acid 1,2-dimethyl-propyl ester;
{2-[3-(3-Methoxy-propionylamino)-phenyl]-3H-imidazo[4,5-b]pyridin-6-yl}-carbamic acid isopropyl ester;
(2-Phenyl-3H-imidazo[4,5-b]pyridin-6-yl)-carbamic acid (E)-1-methyl-but-2-enyl ester;
(2-Phenyl-3H-imidazo[4,5-b]pyridin-6-yl)-carbamic acid 1,2-dimethyl-allyl ester;
{2-[4-(2-Diethylamino-ethoxy)-phenyl]-3H-imidazo[4,5-b]pyridin-6-yl}-carbamic acid isopropyl ester;
2-[3-(2-Methoxy-ethoxy)-phenyl]-3H-imidazo[4,5-b]pyridin-6-yl}-carbamic acid isopropyl ester;
{2-[4-(2-Methoxy-ethoxy)-phenyl]-3H-imidazo[4,5-b]pyridin-6-yl}-carbamic acid isopropyl ester;
[2-(3-Nitro-phenyl)-3H-imidazo[4,5-b]pyridin-6-yl]-carbamic acid isopropyl ester;
[2-(4-Morpholin-4-yl-phenyl)-3H-imidazo[4,5-b]pyridin-6-yl]-amic acid isopropyl ester;
{2-[4-(4-Methyl-piperazin-1-yl)-phenyl]-3H-imidazo[4,5-b]pyridin-6-yl}-carbamic acid isopropyl ester;
{2-[3-(2-Hydroxy-ethyl)-phenyl]-3H-imidazo[4,5-b]pyridin-6-yl}-carbamic acid isopropyl ester;
[2-(4-Nitro-phenyl)-3H-imidazo[4,5-b]pyridin-6-yl]-carbamic acid isopropyl ester;
[2-(4-Sulfamoyl-phenyl)-3H-imidazo[4,5-b]pyridin-6-yl]-carbamic acid isopropyl ester;
[2-(4-Methylsulfanyl-phenyl)-3H-imidazo[4,5-b]pyridin-6-yl]-carbamic acid isopropyl ester;
[2-(3-Amino-phenyl)-3H-imidazo[4,5-b]pyridin-6-yl]-carbamic acid isopropyl ester;
[2-(4-Amino-phenyl)-3H-imidazo[4,5-b]pyridin-6-yl]-carbamic acid isopropyl ester;
[2-(3-Acetylamino-phenyl)-3H-imidazo[4,5-b]pyridin-6-yl]-carbamic acid isopropyl ester;
[2-(3-Methanesulfonylamino-phenyl)-3H-imidazo[4,5-b]pyridin-6-yl]-carbamic acid isopropyl ester;
[2-(3-Methylsulfinyl-phenyl)-3H-imidazo[4,5-b]pyridin-6-yl]-carbamic acid isopropyl ester;
[2-(3-Methylsulfonyl-phenyl)-3H-imidazo[4,5-b]pyridin-6-yl]-carbamic acid isopropyl ester;
[2-(4-Methanesulfonyl-phenyl)-3H-imidazo[4,5-b]pyridin-6-yl]-carbamic acid isopropyl ester;
[2-(4-Methanesulfinyl-phenyl)-3H-imidazo[4,5-b]pyridin-6-yl]-carbamic acid isopropyl ester;
[2-(3,4-Difluoro-phenyl)-3H-imidazo[4,5-b]pyridin-6-yl]-carbamic acid isopropyl ester;
(2-{4-[Bis-(2-methoxy-ethyl)-amino]-3-fluoro-phenyl}-3H-imidazo[4,5-b]pyridin-6-yl)-carbamic acid isopropyl ester;
3-(6-Isopropoxycarbonylamino-3H-imidazo[4,5-b]pyridin-2-yl)-benzoic acid;
{2-[3-(2-Methoxy-I-methoxymethyl-ethylcarbamoyl)-phenyl]-3H-imidazo[4,5-b]pyridin-6-yl}-carbamic acid isopropyl ester; and
{2-[3-(3-Methoxy-propylcarbamoyl)-phenyl]-3H-imidazo[4,5-b]pyridin-6-yl}-carbamic acid isopropyl ester.

7. A compound according to claim 1, wherein:
$R^1$ is a heteroaryl group optionally substituted one or two times with chlorine, heterocyclyl or —Z-alkyl; and the alkyl groups are optionally substituted one or two times by alkoxy;
Z is a single bond or —NR—;
R is hydrogen;
$R^2$ is alkyl; and
A is =N—.

8. A compound according to claim 7 selected from the group consisting of:

(2-Thiophen-2-yl-3H-imidazo[4,5-b]pyridin-6-yl)-carbamic acid isopropyl ester;
(2-Thiophen-3-yl-3H-imidazo[4,5-b]pyridin-6-yl)-carbamic acid isopropyl ester;
[2-(2-Methyl-pyridin-4-yl)-3H-imidazo[4,5-b]pyridin-6-yl]-carbamic acid isopropyl ester;
[2-(6-Methyl-pyridin-3-yl)-3H-imidazo[4,5-b]pyridin-6-yl]-carbamic acid isopropyl ester;
[2-(1H-Benzoimidazol-5-yl)-3H-imidazo[4,5-b]pyridin-6-yl]-carbamic acid isopropyl ester;
[2-(2-Chloro-pyridin-4-yl)-3H-imidazo[4,5-b]pyridin-6-yl]-carbamic acid isopropyl ester; and
{2-[2-(3-Methoxy-propylamino)-pyridin-4-yl]-3H-imidazo[4,5-b]pyridin-6-yl}-carbamic acid isopropyl ester.

9. A composition comprising a compound according to claim 1 and a pharmaceutically acceptable adjuvant.

* * * * *

UNITED STATES PATENT AND TRADEMARK OFFICE
CERTIFICATE OF CORRECTION

PATENT NO. : 7,786,113 B2  Page 1 of 1
APPLICATION NO. : 11/793750
DATED : August 31, 2010
INVENTOR(S) : Honold et al.

It is certified that error appears in the above-identified patent and that said Letters Patent is hereby corrected as shown below:

Claim 6, column 58, line 28, delete "{2-[3-(2-Methoxy-I"
and insert -- {2-[3-(2-Methoxy-1 --

Signed and Sealed this

Fourteenth Day of December, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ala Glu Glu Glu Ile Tyr Gly Glu Phe Glu Ala Lys Lys Lys Lys
1               5                   10                  15